(12) United States Patent
Freed et al.

(10) Patent No.: US 10,327,441 B2
(45) Date of Patent: *Jun. 25, 2019

(54) MODULATION OF CALCIUM ION HOMEOSTASIS IN HARVESTED TRANSPLANTABLE HEARTS

(71) Applicant: TEVOSOL, INC., Edmonton (CA)

(72) Inventors: Darren Freed, Edmonton (CA); Christopher White, Edmonton (CA); Larry Hryshko, Winnipeg (CA)

(73) Assignee: TEVOSOL, INC., Edmonton (CA)

( * ) Notice: Subject to any disclaimer, the term of this patent is extended or adjusted under 35 U.S.C. 154(b) by 76 days.

This patent is subject to a terminal disclaimer.

(21) Appl. No.: 15/302,593

(22) PCT Filed: Apr. 10, 2015

(86) PCT No.: PCT/CA2015/050297
§ 371 (c)(1),
(2) Date: Oct. 7, 2016

(87) PCT Pub. No.: WO2015/154193
PCT Pub. Date: Oct. 15, 2015

(65) Prior Publication Data
US 2017/0020127 A1    Jan. 26, 2017

Related U.S. Application Data

(60) Provisional application No. 61/978,132, filed on Apr. 10, 2014.

(51) Int. Cl.
*A01N 1/02* (2006.01)

(52) U.S. Cl.
CPC .................................. *A01N 1/0226* (2013.01)

(58) Field of Classification Search
CPC ................................................. A01N 1/0226
See application file for complete search history.

(56) References Cited

U.S. PATENT DOCUMENTS

| | | | |
|---|---|---|---|
| 5,405,742 | A | 4/1995 | Taylor |
| 5,407,793 | A | 4/1995 | Del Nido et al. |
| 6,524,785 | B1 | 2/2003 | Cozzone et al. |
| 2003/0124503 | A1 | 7/2003 | Olivencia-Yurvati et al. |
| 2005/0202394 | A1 | 9/2005 | Dobson |
| 2006/0034941 | A1 | 2/2006 | Dobson |
| 2012/0077771 | A1 | 3/2012 | Fallouh |
| 2014/0011745 | A1 | 1/2014 | Dobson |

FOREIGN PATENT DOCUMENTS

WO        01/01774 A1    1/2001

OTHER PUBLICATIONS

Jakobsen et al.,The Journal of Thoracic and Cardiovascular Surgery, 2013, vol. 145, Issue 3, pp. 812-818.*
Rudd et al., The Journal of Thoracic and Cardiovascular Surgery, 2009, vol. 137, p. 198-207.*
Gao et al., Circulation Research. 1997, vol. 80, p. 393-399.*
Ebel et al., British Journal of Anaesthesia, 2001, vol. 86, No. 6, p. 846-852.*
Ely et al., Circulation, 1992, vol. 85, No. 3, p. 893-904.*
Unitslab.com, Online convertor, Lidocaine, retrieved on Jul. 18, 2018.*
Examination Report No. 1 dated May 7, 2018 in related Australian Patent Application No. 2015336862.
Rudd, D.M. et al., "Eight Hours of Cold Statis Storage with Adenosine and Lidocaine (Adenocaine) Heart Preservation Solutions: Toward Therapeutic Suspended Animation" J. Thorac. Cardiovasc. Surg. vol. 142(6), pp. 1552-1561 Dec. 2011.
International Search Report dated Jul. 13, 2015 in PCT/CA2015/050297.
International Preliminary Report on Patentability dated Oct. 12, 2016 in PCT/CA2015/050297.
Taylor, et al., "Registry of the International Society for Heart and Lung Transplantation: Twenty-sixth Official Adult Heart Transplant Report-2009", J. Heart Lung Transplant, 2009, vol. 28(10), pp. 1007-1022.
Extended European Search Report dated Oct. 24, 2017 in related EP Patent Application No. 15775970.5 0.
G. Dobson et al., "Adenosine and lidocaine: A new concept in nondepolarizing surgical myocardial arrest, protection, and preservation", Journal of Thoracic and Cardiovascular Surgery, Mosby-Year Book, 2004, vol. 127(3), pp. 794-805.
C. White et al., "Impact of Reperfusion Calcium and pH on the resuscitation of hearts donated after circulatory death", The Annals of Thoracic Surgery, 2017, vol. 103(1), pp. 122-130.
Written Opinion dated Jul. 13, 2015 in PCT/CA2015/050297.
International Preliminary Report on Patentability dated Feb. 15, 2017 in PCT/CA2015/051084.
International Search Report dated Feb. 5, 2016 in PCT/CA2015/051084.
Written Opinion dated Feb. 5, 2016 in PCT/CA2015/051084.
Baker, "Calcium content of St. Thomas' II cardioplegic solution damages ischemic immature myocardium", The Annals of Thoracic Surgery, 1991, vol. 52(4), pp. 993-999.
Robinson et al., "Lowering the calcium concentration in St. Thomas' Hospital cardioplegic solution improves protection during hypothermic ischemia", J. Thorac. Cardiovasc. Surg., 1991, vol. 101(2), pp. 314-325.

(Continued)

Primary Examiner — Kade Ariani

(57) ABSTRACT

An oxygenated cardioplegic composition for immediate reperfusion of a donor heart after its procurement. The composition comprises an adenosine-lidocaine mixture for causing immediate cessation of the heart's systolic function upon contact; a normokalemic concentration of potassium ions; a concentration of $Ca^{2+}$ ions selected to maintain the intracellular level of $Ca^{2+}$ ions in the harvested heart muscle cells at about $10^{-4}$ mmol/L; and a pH of 6.9. The oxygenated cardioplegic composition is pre-warmed to about 35° C. and then used for immediate reperfusion of a donor heart for at least three minutes after its procurement.

6 Claims, 31 Drawing Sheets

(56) References Cited

OTHER PUBLICATIONS

Muhlbacher et al., "Preservation solutions for transplantation", Transplant Proc., 1999, vol. 31(5), pp. 2069-2070.
Examination Report dated Mar. 14, 2018 in related Australian Patent Application No. 2015245903.
Extended European Search Report dated Mar. 9, 2018 in related EP Patent Application No. 15853016.2.
O'Blenes et al., "Protecting the aged heart during cardian surgery: The potential benefits of del Nido cardioplegia", Journal of Thoracic and Cardiovascular Surgery, 2011, vol. 141(3), pp. 762-770.
Takemoto, et al., "The reciprocal protective effects of magnesium and calcium in hyperkalemic cardioplegic solutions on ischemic myocardium", Basic Research in Cardiology, 1992, vol. 87(1), pp. 559-569.
Hearse, et al., "Protection of the myocardium during ischemic arrest. Dose response curves for procaine and lignocaine in cardioplegic solutions", Journal of Thoracic and Cardiovascular Surgery, 1981, vol. 81(6), pp. 873-879.
White, et al., "Impact of initial reperfusion temperature on the functional recovery of DCD hearts", Journal of Heart and Lung Transplantation, 2014, vol. 33(4 Supplement), p. S109.
White et al., "Impact of initial acidic reperfusion on the functional recovery of DCD hearts during ex vivo heart perfusion", Canadian Journal of Cardiology, 2014, vol. 30, pp. S252-S252.
White et al., "Impact of initial acidic reperfusion on the functional recovery of DCD hearts during ex vivo heart perfusion", Journal of Heart and Lung Transplantation, 2015, vol. 34(4 Supplement), pp. S269-S270.
Non-final Office Action dated Aug. 7, 2018 in related U.S. Appl. No. 15/521,484.

\* cited by examiner

US 10,327,441 B2

MODULATION OF CALCIUM ION HOMEOSTASIS IN HARVESTED TRANSPLANTABLE HEARTS

CROSS-REFERENCE TO RELATED APPLICATION

This application is a national filing of International Application No. PCT/CA2015/050297, filed on Apr. 10, 2015, entitled "Modulation of Calcium Ion Homeostasis in Harvested Transplantable Hearts," having as inventors Darren Freed and Christopher White, which claims benefit of U.S. Provisional Application No. 61/978,132, filed on Apr. 10, 2014.

FIELD OF THE INVENTION

The present invention pertains to post-harvest maintenance of harvested hearts prior to their transplantation into recipient subjects, and more particularly, to perfusate compositions and their use for extended ex vivo maintenance of harvested hearts.

BACKGROUND OF THE INVENTION

Heart failure affects 10% of North Americans and is the leading hospital discharge diagnosis. The diagnosis of heart failure is accompanied by a survival outlook that is comparable to a major cancer. There are limited rehabilitation options available to patients who are suffering with heart failure, and few strategies actually re-power the heart. Cardiac transplantation remains the gold-standard therapeutic intervention for patients with end-stage heart failure, with an increasing number of individuals being added to the transplant wait list every year. However, wider application of this life-preserving intervention is limited by the availability of donors. Data from the International Society of Heart and Lung Transplantation Registry shows that cardiac transplantation is in progressive decline in suitable donors (2007, *Overall Heart and Adult Heart Transplantation Statistics*). Two hundred and fifty eight Canadians have died during the last decade (2000-2010; Heart and Stroke Foundation of Canada) while waiting for heart transplantation. Similarly, in the United States, 304 patients died in 2010 alone while waiting for heart transplantation (Organ Procurement and Transplantation Network, US Dept. of Health & Human Services). This phenomenon is primarily due to a shortage of suitable organ donors, and is being experienced across the globe.

Time is of the essence for removal of a heart from a donor and its successful transplantation into a recipient. The following principles generally apply for optimal donor heart preservation for the period of time between removal from the donor and transplantation: (i) minimization of cell swelling and edema, (ii) prevention of intracellular acidosis, (iii) prevention of injury caused by oxygen free radicals, and (iv) provision of substrate for regeneration of high-energy phosphate compounds and ATP during reperfusion. The two main sources of donor hearts for transplantation are breathing patients who have suffered irreversible loss of brain function as a result of blunt head trauma or intracerebral hemorrhage and are classified as "brainstem-dead" donors, and patients who have suffered circulatory death and are referred to as "non-heart-beating" or alternatively as "cardiac dead" donors or alternatively, donors after circulatory death (DCDs), Brainstem-dead organ donors can be maintained under artificial respiration for extended periods of time to provide relative hemodynamic stability up throughout their bodies until the point of organ retrieval. Therefore, cardiac perfusion is uncompromised and organ functionality is theoretically maintained. However, brainstem death itself can profoundly affect cardiac function. The humoral response to brainstem death is characterized by a marked rise in circulating catecholamines. Physiological responses to this "catecholamine storm" include vasoconstriction, hypertension and tachycardia, all of which increase myocardial oxygen demand. In the coronary circulation Significant increased levels of catecholamine circulating throughout the vascular system induce vasoconstriction which in turn, compromises myocardial oxygen supply and can lead to subendocardial ischemia. This imbalance between myocardial oxygen supply and demand is one factor implicated in the impairment of cardiac function observed following brainstem death (Halejcio-Delophont et al., 1998, *Increase in myocardial interstitial adenosine and net lactate production in brain-dead pigs: an in vivo microdialysis study*. Transplantation 66(10):1278-1284; Halejcio-Delophont et al., 1998, *Consequences of brain death on coronary blood flow and myocardial metabolism*. Transplant Proc. 30(6):2840-2841). Structural myocardial damage occurring after brainstem death is characterized by myocytolysis, contraction band necrosis, sub-endocardial hemorrhage, edema and interstitial mononuclear cell infiltration (Baroldi et al., 1997, *Type and extent of myocardial injury related to brain damage and its significance in heart transplantation: a morphometric study*. J. Heart Lung Transplant 16(10):994-1000). In spite of no direct cardiac insult, brainstem-dead donors often exhibit reduced cardiac function and the current views are that only 40% of hearts can be recovered from this donor population for transplantation.

Numerous perfusion apparatus, systems and methods have been developed for ex vivo maintenance and transportation of harvested organs. Most employ hypothermic conditions to reduce organ metabolism, lower organ energy requirements, delay the depletion of high energy phosphate reserves, delay the accumulation of lactic acid, and retard morphological and functional deteriorations associated with disruption of oxygenated blood supply. Harvested organs are generally perfused in these systems with preservative solutions comprising antioxidants and pyruvate under low temperatures to maintain their physiological functionality.

The short-comings of hypothermic apparatus, systems and methods have been recognized by those skilled in these arts, and alternative apparatus, systems and methods have been developed for preservation and maintenance of harvested organs at temperatures in the range of about 25° C. to about 35° C., commonly referred to as "normothermic" temperatures. Normothermic systems typically use perfusates based on the Viaspan formulation (also known as the University of Wisconsin solution or UW solution) supplemented with one or more of serum albumin as a source of protein and colloid, trace elements to potentiate viability and cellular function, pyruvate and adenosine for oxidative phosphorylation support, transferrin as an attachment factor; insulin and sugars for metabolic support, glutathione to scavenge toxic free radicals as well as a source of impermeant, cyclodextrin as a source of impermeant, scavenger, and potentiator of cell attachment and growth factors, a high $Mg^{++}$ concentration for microvessel metabolism support, mucopolysaccharides for growth factor potentiation and hemostasis, and endothelial growth factors (Viaspan comprises potassium lactobionate, $KH_2PO_4$, $MgSO_4$, raffinose, adenosine, glutathione, allopurinol, and hydroxyethyl starch). Other normothermic perfusation solutions have been developed and used (Muhlbacher et al., 1999, *Preservation solutions for transplantation*. Transplant Proc. 31(5):2069-2070). While harvested kidneys and livers can be maintained beyond twelve hours in normothermic systems, it has become apparent that normothermic bathing, and maintenance of harvested hearts by pulsed perfusion beyond 12 hours results in deterioration and irreversible debilitation of the hearts' physiological functionality. Another disadvantage of using normothermic continuous pulsed perfusion systems for maintenance of harvested hearts is the time required to excise the heart from a donor, mount it into the nomothermic perfusion system and then initiate and stabilize the perfusion process. After the excised heart has been stabilized, its physiological functionality is determined and if transplantation criteria are met, then the excised heart is transported as quickly as possible to a transplant facility.

In the case of brain-stem dead donors, the heart generally is warm and beating when it is procured. It is then stopped, cooled, and put on ice until it is transplanted. Chilling the harvested heart reduces its metabolic activity and related demands by about 95%. However, some metabolic activity continues with the consequence that the heart muscle begins to die, and clinical data has shown that once the period of chilling of a harvested heart is prolonged beyond 4 hours, the risk of 1 year mortality post-transplant starts to rise. For example, risk of death at one-year post-transplant for a recipient receiving a heart that has been preserved by chilling for six hours more than doubles compared to a recipient receiving a heart that has been chilled for less than 1 hour (Taylor et al., 2009, *Registry of the International Society for Heart and Lung Transplantation: Twenty-sixth Official Adult Heart Transplant Report*—2009. JHLT 28(10): 1007-1022).

Well-defined criteria have been developed for harvesting organs for transplantation from non-heart-beating donors (Kootstra et al., 1995, *Categories of non-heart-beating donors*. Transplant Proc. 27(5):2893-2894; Bos, 2005, *Ethical and legal issues in non-heart-beating organ donation*. Transplantation, 2005. 79(9): p. 1143-1147). Non-heart-beating donors have minimal brain function but do not meet the criteria for brainstem death and therefore, cannot be legally declared brainstem dead. When it is clear that there is no hope for meaningful recovery of the patient, the physicians and family must be in agreement to withdraw supportive measures. Up to this point in care, non-heart-beating patients are often supported with mechanical ventilation as well as intravenous inotropic or vasopressor medication. However, only those with single system organ failure (neurologic system) can be considered for organ donation. Withdrawal of life support, most commonly the cessation of mechanical ventilation, is followed by anoxic cardiac arrest after which, the patient must remain asystolic for five minutes before organ procurement is allowed. Consequently, non-heart-beating donors are necessarily exposed to variable periods of warm ischemia after cardiac arrest which may result in various degrees of organ damage. However, provided that the time duration of warm ischemia is not excessive, many types organs, i.e., kidneys, livers, and lungs, harvested from non-heart-beating donors are able to recover function after transplantation with success rates that approximate those for transplanted organs from brainstem-dead beating donors. While hearts harvested from brain-dead donors are exposed to an ischemic period limited to the time from organ procurement to transplant, hearts harvested from donors after cardiac death are exposed to much greater ischemic insult events including a hypoxemic arrest event, warm ischemic injury occurring during the mandatory five-minute stand-off period before organ harvesting may be commenced, and further ischemia injury occurring during subsequent reperfusion of the heart after it is harvested. Because of the extent of ischemic damage that occurs during the time delays before organ harvesting commences, hearts from donors after cardiac death are not used for transplantation into recipients.

SUMMARY OF THE INVENTION

The exemplary embodiments of the present disclosure relate to perfusate solutions for immersion and bathing of a harvested heart therein while being concurrently flowed through the heart.

Some exemplary embodiments of the present disclosure pertain to use of perfusate solutions for ex vivo maintenance of harvested hearts to minimize and remediate post-harvest ischemic damage therein.

Some exemplary embodiments of the present disclosure pertain to methods for ex vivo maintenance of harvested hearts to minimize the occurrence and extent of post-harvest ischemic damage therein.

BRIEF DESCRIPTION OF THE DRAWINGS

The present invention will be described in conjunction with reference to the following drawings in which:

FIG. 7(A) is a micrograph of a section through a harvested heart reperfused at 5° C. showing swollen endothelial cells in the capillary, while FIG. 7(B) is a micrograph of a section through a harvested heart reperfused at 35° C. showing normal endothelial cells in the capillary;

DESCRIPTION OF THE INVENTION

Figure 1:
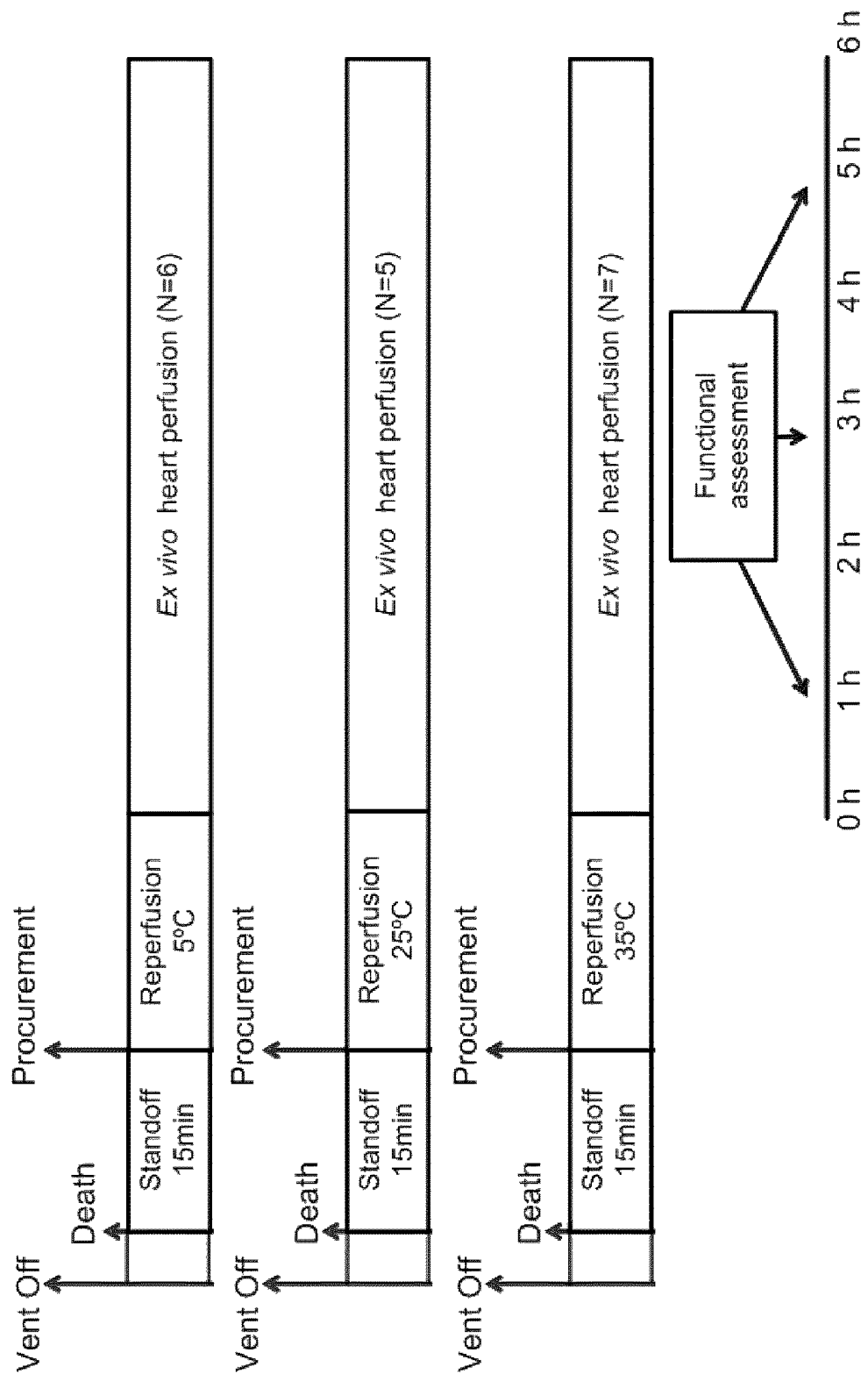
FIG. 1 is a schematic flowchart outlining the experimental protocols used in Example 1.

Unless otherwise defined, all technical and scientific terms used herein have the same meaning as commonly understood by one of ordinary skill in the art to which this invention belongs. In order that the invention herein described may be fully understood, the following terms and definitions are provided herein.

The word "comprise" or variations such as "comprises" or "comprising" will be understood to imply the inclusion of a stated integer or groups of integers but not the exclusion of any other integer or group of integers.

The term "about" or "approximately" means within 20%, preferably within 10%, and more preferably within 5% of a given value or range.

The term "modulate" as used herein means to regulate the operation of a device by increasing a signal to the device in order to increase an output by the device, or by decreasing a signal to the device in order to decrease an output by the device.

The term "afterload" means the mean tension produced by a chamber of the heart in order to contract. It can also be considered as the 'load' that the heart must eject blood against. Afterload is therefore a consequence of aortic large vessel compliance, wave reflection and small vessel resistance (left ventricular afterload) or similar pulmonary artery parameters (right ventricular afterload).

The term "preload" refers to the stretching of a single cardiac myocyte immediately prior to contraction and is therefore related to the sarcomere length. Since sarcomere length cannot be determined in the intact heart, other indices of preload such as ventricular end diastolic volume or pressure are used. As an example, preload increases when venous return is increased.

The term "cardiac myocyte" means a cardiac muscle cell.

The term "stroke volume" (SV) means the volume of blood ejected by the right/left ventricle in a single contraction. It is the difference between the end diastolic volume (EDV) and the end systolic volume (ESV). Mathematically, SV=EDV−ESV. The stroke volume is affected by changes in preload, afterload and inotropy (contractility). In normal hearts, the SV is not strongly influenced by afterload whereas in failing hearts, the SV is highly sensitive to afterload changes.

The term "stroke work" (SW) refers to the work performed by the left or right ventricle to eject the stroke volume into the aorta or pulmonary artery, respectively. The area enclosed by the pressure/volume loop is a measure of the ventricular stroke work, which is a product of the stroke volume and the mean aortic or pulmonary artery pressure (afterload), depending on whether one is considering the left or the right ventricle.

The term "ejection fraction" (EF) means the fraction of end diastolic volume that is ejected out of the ventricle during each contraction. Mathematically, EF=SV/EDV. Healthy ventricles typically have ejection fractions greater than 0.55. Low EF usually indicates systolic dysfunction and severe heart failure can result in EF lower than 0.2. EF is also used as a clinical indicator of the inotropy (contractility) of the heart. Increasing inotropy leads to an increase in EF, while decreasing inotropy decreases EF.

The term "end systolic pressure volume relationship" (ESPVR) describes the maximal pressure that can be developed by the left ventricle at any given left ventricular volume, or alternatively, by the right ventricle at any given right ventricular volume. This implies that the PV loop cannot cross over the line defining ESPVR for any given contractile state. The slope of ESPVR (Ees) represents the end-systolic elastance, which provides an index of myocardial contractility. The ESPVR is relatively insensitive to changes in preload, afterload and heart rate. This makes it an improved index of systolic function over other hemodynamic parameters like ejection fraction, cardiac output and stroke volume. The ESPVR becomes steeper and shifts to the left as inotropy (contractility) increases. The ESPVR becomes flatter and shifts to the right as inotropy decreases.

The term "preload recruitable stroke work relationship" (PRSW) means a measure of cardiac contractility, and is the linear relationship between SW and EDV.

The term "pressure-volume area" (PVA) means the total mechanical energy generated by ventricular contraction. This is equal to the sum of the stroke work (SW), encompassed within the PV loop, and the elastic potential energy (PE). Mathematically, PVA=PE+SW.

The term "dP/dt max" is a quantified measure of the global contractility of the left ventricle. The greater the contractile force exerted during systole, the greater the rate of increase in left ventricular pressure.

The term "dP/dt min" is a quantified measure of the relaxation of the left ventricle during diastole.

As used herein, the term "DND" means donor after circulatory death.

As used herein, the term "DBD" means donor after brain death.

The term "Langendorff perfusion" refers to a method of perfusing an excised heart with a nutrient-rich oxygenated solution in a reverse fashion via the aorta. The backwards pressure causes the aortic valve to shut thereby forcing the solution into the coronary vessels, which normally supply the heart tissue with blood. This feeds nutrients and oxygen to the cardiac muscle, allowing it to continue beating for several hours after its removal from the animal.

The term "working heart" as used herein, refers to clinical ex vivo coronary perfusion throughout a excised heart by ventricular filling via the left atrium and ejection from the left ventricle via the aorta driven by the heart's contractile function and regular cardiac rhythm. The excised heart is attached by cannulae to a perfusate reservoir and circulatory pumps in a Langendoff preparation. The flow of perfusate through the excised heart in "working heart" mode is in the direction opposite to the flow of perfusate during Langedorff perfusion.

The term "ischemia" means a condition that occurs when blood flow and oxygen are kept from the heart.

The term "reperfusion" as used herein means the concurrent immersion of a harvested heart in a constantly flowing supply an oxygen-rich solution perfusate solution while optionally, concurrently pumping the perfusate solution through the heart.

The term "reperfusion injury" as used herein refers to tissue damage in a harvested heart that occurs when a supply of oxygen via a perfusate solution is provided to the tissue after a period of ischemia or lack of oxygen. The absence of oxygen and nutrients from heart during the ischemic period creates a condition in which the restoration of circulation results in inflammation and oxidative damage through the induction of oxidative stress rather than restoration of normal function.

The term "cardioplegia" as used herein means an intentional and temporary cessation of cardiac activity by arresting or stopping the beating of a heart. Cardioplegia can be imposed on a beating heart by directly by chilling and/or by chilling and a concurrent administration of a solution containing one or more chemicals that will cause paralysis of the heart muscle.

The term "cardioplegic solution" as used herein means a solution containing chemical components that solution cause asystole of the heart i.e., heart paralysis.

The term "homeostasis" as used herein means the maintenance of a stable and relative constant metabolic equilibrium within and among the muscle cells of a harvested heart.

The term "normokalemic" as used herein means having or characterized by a normal concentration of potassium in the blood. Normal serum potassium levels are in a range between 3.5 mEq/L and 5.0 mEq/L.

The term "hyperkalemic" as used herein means having or characterized by a concentration of potassium that is significantly elevated aver a normokalemic concentration. A hyperkalemic concentration includes any potassium concentration in excess of 6.0 mEq/L.

The term "normothermic" as used herein means having a normal body temperature, which is an average of about 37° C.

The term "hypothermic" as used herein means a temperature that is less than about 20° C.

The medically prescribed events that must occur for ethical procurement of transplantable hearts from brain-dead donors and from donors with cardiac death, inevitably cause an occurrence of cardiac arrest and a sequence of ischemic events resulting in damage to the heart muscles, and cannot be modified.

Ischemia is accompanied by significant changes in ion exchange patterns into and out of heart muscle cells as a consequence in the loss of oxygen supply. As the availability of oxygen decreases and stops, the metabolism of the heart muscle cells shifts from aerobic to anaerobic with an immediate consequence of rapidly decreasing intracellular pH levels which in turn, results in increasing amounts of $H^+$ ions excreted from within the muscle cells into the extracellular spaces while concurrently, the ion potential across the cellular membranes is increasingly deactivated due to loss of ATP thereby significantly reducing $Na^+/Ca^{2+}$ ion exchange. The ultimate result is an increasing overload in the intracellular $Ca^{2+}$ ion levels. The increased levels of intracellular $Ca^{2+}$ ion levels activate $Ca^{2+}$-dependent proteases which disrupt cell structure resulting in cell death. The severity of such damage increases with the duration of the ischemic conditions.

Ischemic damage occurring during the procurement of a donor heart may be reduced by reperfusion of the harvested heart as soon as possible after its harvest in blood or a blood replacement product exemplified by Viaspan and CELSIOR® (CELSIOR is a registered trademark of Genzyme Corp., Cambridge, Mass., USA). Reperfusion causes a prompt recovery i.e. increase in the extracellular pH resulting in robust excretion of $H^+$ ions which reverses the $Na^+/Ca^{2+}$ ion exchange across the heart cell membranes resulting in "reverse mode" excretion of accumulated intracellular $Na^+$ ions accompanied by an influx of $Ca^{2+}$ ions accompanied by recovery of ATP synthesis, followed by a subsequent re-excretion of $Ca^{2+}$ ions. However, although reperfusion may re-establish aerobic respiration and metabolism in harvested hearts, reperfusion commonly results in further damage (i.e., reperfusion injury) to the heart muscle cells. For example, the immediate increase in intracellular pHs results in the generation of reactive oxygen species that activate subcellular signals that in turn activate inflammatory cascades that cause apoptosis and cytokine release. Additionally, reactive oxygen species directly disrupt DNA structures and protein structures thereby causing cell death. Another problem associated with reperfusion is that it is very difficult to modulate the intracellular levels of $Ca^{2+}$ ions during the perfusion process with the result that reperfusion further adds to the intracellular overload of $Ca^{2+}$ ions in heart muscle cells.

Contraction of a heart while the heart muscle cells are overloaded with intracellular levels of $Ca^{2+}$ ions during reperfusion inevitably results in the occurrence of a disruptive type of necrosis, termed contraction band necrosis as a result of massive myofibril contraction after reperfusion-induced calcium re-entry. This form of reperfusion injury is considered to be the most severe.

Accordingly, the rationale for chilling donor hearts immediately after their procurement and during reperfusion, is to reduce metabolic activity within the heart muscle cells as quickly as possible to minimize the extent of ischemic damage caused by intracellular overload of $Ca^{2+}$ ions, to minimize the generation of reactive oxygen species during reperfusion, and to minimize a subsequent intracellular overload of $Ca^{2+}$ ions during reperfusion.

We have discovered that myocardial injury to donor hearts may be minimized by a strategy focused on maintaining calcium ion homeostasis in and about the heart during the harvesting and the reperfusion processes. Our strategy comprises two components wherein the first component is an oxygenated cardioplegic composition for use as perfusate solution during procurement of a harvested heart and for a period of time immediately after harvest during which the harvested heart is reperfused for at least 3 minutes. The at-least 3-minute reperfusion period immediately after the heart is harvested, is referred to as the immediate—early (IE) period. The second component of our strategy is to avoid chilling the heart during procurement process and during the post-harvest reperfusion period, and instead maintain normothermic conditions during harvest, during IE reperfusion, and during subsequent ex vivo maintenance of the harvested heart.

Accordingly, one exemplary embodiment of the present disclosure pertains to an exemplary cardioplegic composition for causing an immediate cessation of a donor heart's rhythmic beating upon its contact with the cardioplegic composition. The cardioplegic composition comprises an adenosine-lidocaine mixture, a normokalemic concentration of potassium ions, a concentration of $Ca^{2+}$ ions selected to maintain the intracellular level of $Ca^{2+}$ ions in the harvested heart's muscle cells at about $10^{-4}$ mmol/L, and a pH of 6.9. A suitable adenosine-lidocaine mixture comprises 300 μmol/L, 325 μmol/L, 350 μmol/L, 375 μmol/L, 400 μmol/L, 425 μmol/L, 450 μmol/L of adenosine and 40 μmol/L, 45 μmol/L, 50 μmol/L, 55 μmol/L, 60 μmol/L, 70 μmol/L, 80 μmol/L, 90 μmol/L of lidocaine. The cardioplegic composition additionally comprises 8.0-12.5 mmol/L of glucose, 120-140 mmol/L of NaCl, 4.0-7.0 mmol/L of KCL, 12.0-16.0 mmol/L of $NaHCO_3$, 0.9-1.4 mmol/L of $NaH_2PO_4$, 0.18-0.26 mmol/L of $CaCl_2$, 11.0-15.0 mmol/L of $MgCl_2$, 7.5-12.5 IU/L of insulin, 100.0-140.0 mmol/L of D-mannitol, 0.75-1.25 mmol/L of pyruvate, and 2.5-3.5 mmol/L of reduced glutathione. A particularly suitable exemplary cardioplegic composition comprises 400 μmol/L of adenosine, 50 μmol/L of lidocaine, 10.0 mmol/L of glucose, 131.8 mmol/L of NaCl, 5.9 mmol/L of KCL, 14.0 mmol/L of $NaHCO_3$, 1.2 mmol/L of $NaH_2PO_4$, 0.22 mmol/L of $CaCl_2$, 13.0 mmol/L of $MgCl_2$, 10.0 IU/L of insulin, 120.0 mmol/L of D-mannitol, 1.0 mmol/L of pyruvate, and 3.0 mmol/L of reduced glutathione. The cardioplegic composition is oxygenated by bubbling a stream of $O_2$ gas through the cardioplegic composition prior to and during its use for bathing and reperfusing a harvested donor.

Another exemplary embodiment of the present disclosure pertains to use of the exemplary oxygenated cardioplegic composition to reperfuse a harvested heart at a normothermic temperature of about 35° C. Accordingly, the exemplary oxygenated cardioplegic composition is warmed to about 35° C. before contacting the heart during procurement and subsequent IE reperfusion for at least 3 minutes after procurement has been completed. After the initial IE reperfusion period in the exemplary oxygenated cardioplegic composition under normothermic conditions, the harvested heart may be resuscitated by installation into a suitable apparatus for ex vivo maintenance of a functioning systolic harvested heart, by interconnection of conduit infrastructures provided within the apparatus with the heart's aorta, pulmonary artery, pulmonary vein, and vena cava, and bathing the excised heart in a constantly flowing perfusate solution comprising oxygenated blood and/or an oxygenated blood replacement solution. Additionally the constantly flowing perfusion solution is flowed through the heart's chambers while it is maintained in the apparatus. Such apparatus are generally configured with: (i) a perfusate pumping system, (ii) flow sensors for monitoring the flow of perfusate to and from the installed heart's aorta, pulmonary artery, pulmonary vein, and vena cava, (iii) an ECG apparatus interconnectable with the excised heart, (v) probes interconnecting the installed heart with instruments for monitoring the excised heart's physiological functionality using load independent indices and load dependent indices, and optionally (vi) pacemakers for initiating and/or maintaining systolic function of the heart.

Use of the exemplary oxygenated cardioplegic composition as disclosed herein will provide a harvested heart with the ionic complement necessary for the ex vivo-maintained heart to continue generating ATP and pumping excess calcium out of the heart muscles cells while keeping the heart in a paralyzed condition i.e., a non-beating asystolic condition, thereby minimizing the potential for occurrence of contraction band necrosis. While not wishing to be bound by any particular theory, it is likely that use of the exemplary oxygenated cardioplegic composition for reperfusion of harvested hearts at normothermic temperatures will facilitate rapid restoration of calcium ion homeostasis and facilitate more rapid recovery and functional operation of the harvested heart after transplantation into a recipient subject.

The following examples are provided to more fully describe the disclosure and are presented for non-limiting illustrative purposes.

EXAMPLES

Example 1

It is apparent that strategies to minimize post-harvest ex vivo trauma and injury to donor hearts requires an understanding of ionic changes that occur in the heart during ischemia and during/after reperfusion.

During ischemia, the heart's metabolism shifts from aerobic to anaerobic with a subsequent production of protons within the cardiac myocytes. The excess protons efflux through the myocyte cell walls in exchange for ingressing $Na^+$ ions through $Na^+/K^+$ pump. As the ATP reserves within the myocytes are depleted, the myocytes become unable to pump the ingressing $Na^+$ ions back out through the $Na^+/K^+$ pump. As a result, as the duration of ischemia progresses, there is an accumulation of: (i) $Na^+$ ions within the myocytes, and (ii) $Na^+$ ions and $H^+$ ions inside and outside the myocytes.

During reperfusion, the $H^+$ ions on the outside of the myocytes are washed away resulting in the occurrence of a large $Na^+/H^+$ gradient across the myocyte walls resulting in a large influx of $Na^+$ ions into the myocytes. The increased concentration of $Na^+$ ions causes the $Na^+/Ca^{2+}$ pump to work in a reverse mode resulting in an influx of $Ca^{2+}$ ions into the myocytes as the $Na^+/Ca^{2+}$ pump attempts to equilibrate the levels of $Na^+$ ions inside and outside of the myocytes. If a $Ca^{2+}$-overloaded myocyte is allowed to contract, a fatal hypercontracture may occur (the hypercontracture is also commonly referred to as "contraction band necrosis"). Consequently, a primary goal of rescusitating a DCD heart is to mitigate a $Ca^{2+}$ ion overload in the myocytes.

Accordingly, our goals were to prevent a harvested DCD heart from contracting by reperfusion with an anesthetic-containing cardioplegic solution while providing the requisite substrates for regenerating ATP so that the reperfused heart could restore its homeostatis by pumping $Na^+$ ions and $Ca^{2+}$ ions and thereby minimize ischemia reperfusion trauma and injury. Because the generation of ATP to provide the energy necessary to exchange ions across the $Na^+/K^+$ pumps and the $Na^+/Ca^{2+}$ pumps, it was our idea that reperfusion of harvested donor hearts would facilitate more rapid restoration of ion homeostatis and recovery of cardiac function. Accordingly, the first study assessed the effects of reperfusion temperature on harvested donor hearts.

Eighteen pigs were separated into three groups and then euthanized following standard protocols and medical ethics procedures following the schematic flowchart shown in FIG. 1.

Six pigs were assigned to the first group. Immediately after procurement of each heart was completed, each heart was installed into a Quest MPS®2 Myocardial Protection System (MPS is a registered trademark of Quest Medical Inc., Allen, Tex., USA) for precise control of the reperfusion pressure and temperature. The harvested hearts from first group of pigs were perfused for 3 minutes with the exemplary oxygenated cardioplegic composition that was chilled to 5° C. prior to commencing the reperfusion process. The aortic perfusion pressure, coronary artery flow, and myocardial temperature were constantly monitored and recorded by the MPS®2 apparatus during the 3-minute initial reperfusion period. Blood gas samples were measured at 0, 30, 60, 120, and 180 seconds of the initial reperfusion period to collect data pertaining to changes occurring the partial pressure of $O_2$ ($PaO_2$), partial pressure of $CO_2$ ($PaCO_2$), pH levels, electrolyte levels, lactate levels among others.

After the initial 3-minute reperfusion period was completed. Each heart was removed from the Quest MPS®2 apparatus and transferred into an ex vivo heart perfusion (EVHP) apparatus where it was perfused with a constantly flowing supply of a blood-STEEN solution mixture (Hb 45 g/L; XVIVO Perfusion Inc., Englewood, Colo., USA) wherein its systolic function was restored and maintained in a Landorff mode at a normothermic temperature of 35° C. for 6 hours. The aortic pressure and heart rate were constantly monitored and processed using the LABCHART® software (LABCHART is a registered trademark of ADInstruments Pty. Ltd., Bella Vista, NSW, Australia). At 1 h, 3 h, and 5 h of perfusion with the blood-STEEN solution mixture in the EVHP apparatus, each heart was transitioned from the Langendorff mode to a working mode by bringing the left atrial pressure from 0 to 8 mmHg and pacing the heart at 100 bpm. Cardiac output, coronary blood flow, aortic root, and coronary sinus blood gases were measured, and cardiac function was assessed with a pressure-volume loop catheter. After these measurements were completed, each heart was immediately returned to the Langendorff mode.

Five pigs were assigned to the second group, and were processed as described above for the first group with the only exception that the IE reperfusion was done with the exemplary oxygenated cardioplegic composition that had been cooled to 25° C. prior to commencing the reperfusion process.

Seven pigs were assigned to the third group, and were processed as described above for the first group with the only exception that the IE reperfusion was done with the exemplary oxygenated cardioplegic composition that had been warmed to 35° C. prior to commencing the reperfusion process.

Figure 2:
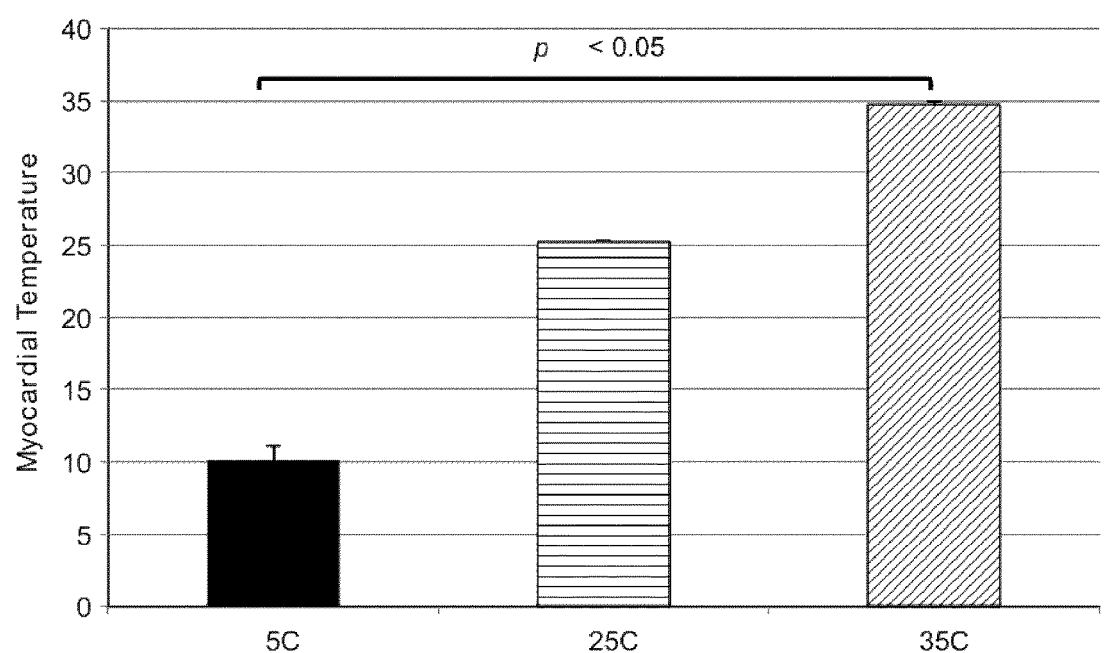
FIG. 2 is a chart showing the myocardial temperature achieved in harvested hearts after an initial 3-minute reperfusion period.

The data in FIG. 2 show that the myocardial temperatures recorded in the hearts receiving the IE reperfusion treatment with the exemplary oxygenated cardioplegic composition chilled to 5° C. dropped to about 10° C. by the end of the 3-min IE reperfusion period. The myocardial temperatures recorded in the hearts that received IE reperfusion with the exemplary oxygenated cardioplegic composition cooled to 25° C., while the myocardial temperatures recorded in the hearts that received normothermic IE reperfusion with the exemplary oxygenated cardioplegic composition were about 35° C.

Figure 3:
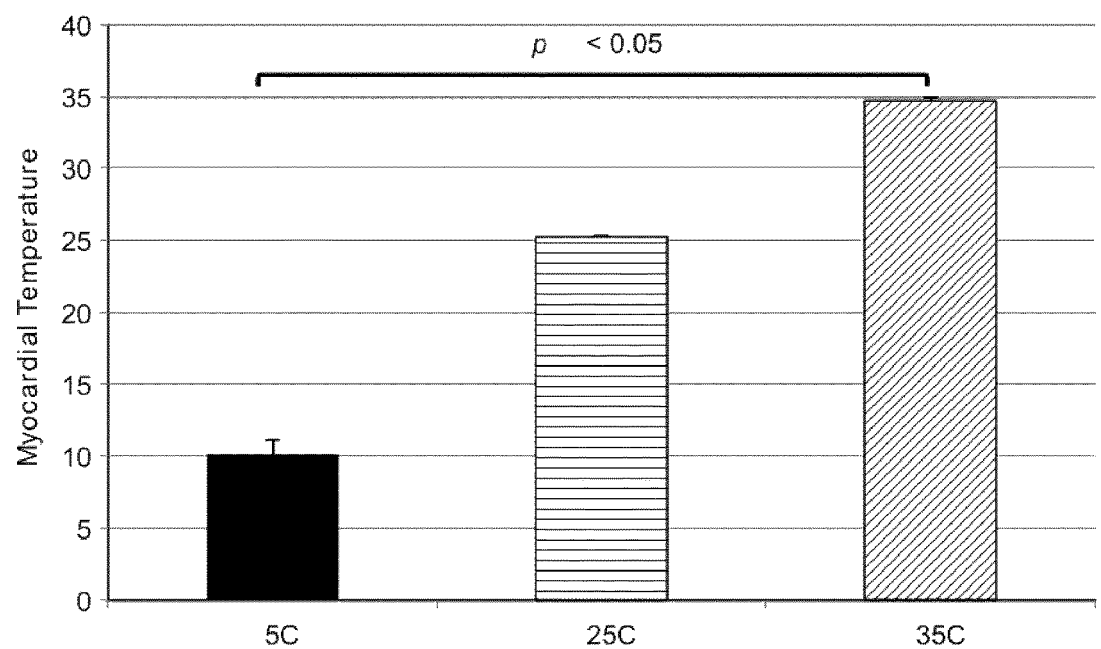
FIG. 3 is a chart showing the effects of temperature on the coronary blood flow through harvested hearts, measured after the initial 3-minute reperfusion period.

FIG. 3 shows that rates of coronary blood flow were reduced by about 15% in hearts that were reperfused with the exemplary oxygenated cardioplegic composition cooled to 25° C. compared to coronary blood flow in hearts that received the normothermic reperfusion with the exemplary oxygenated cardioplegic composition. However, rates of coronary blood flow were reduced by nearly 50% in hearts that were reperfused with the exemplary oxygenated cardioplegic composition chilled 5° C. compared to coronary blood flow in hearts that received the normothermic reperfusion with the exemplary oxygenated cardioplegic composition.

Figure 4:
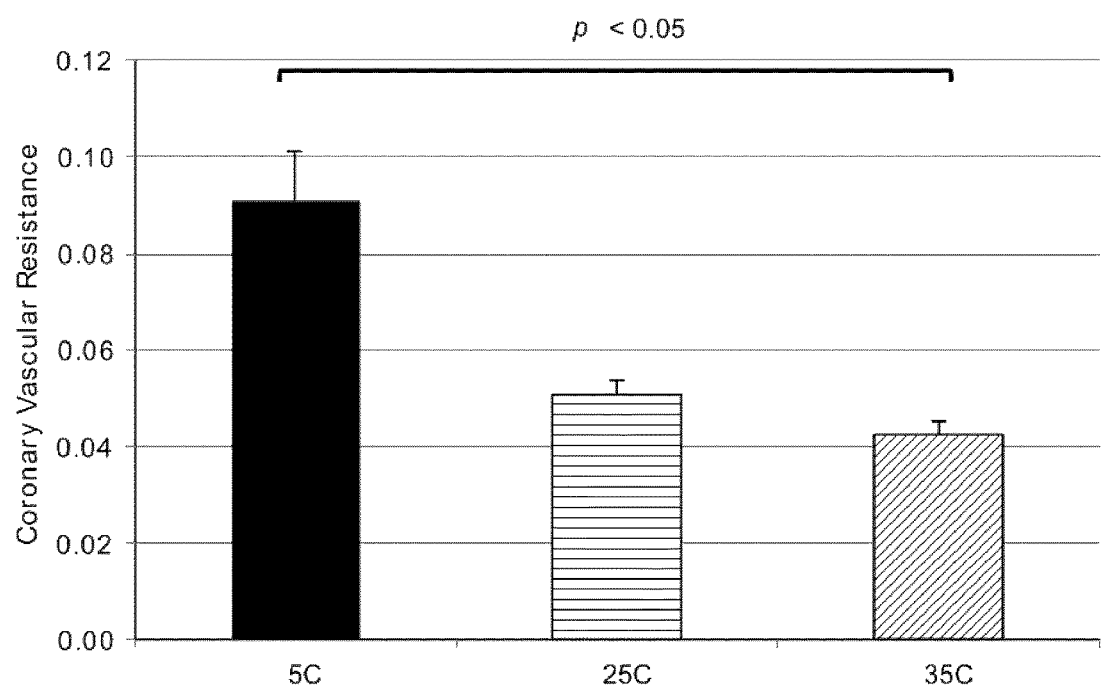
FIG. 4 is a chart showing the effects of temperature on coronary vascular resistance to blood flow through harvested hearts, measured after the initial 3-minute reperfusion period.

FIG. 4 shows that the coronary vascular resistance in hearts reperfused with the cooled oxygenated cardioplegic composition dropped by about 40% compared to the hearts reperfused with the normothermic oxygenated cardioplegic composition, while the chilled oxygenated cardioplegic composition caused a reduction of more than 50% in the coronary vascular resistance.

Figure 5:
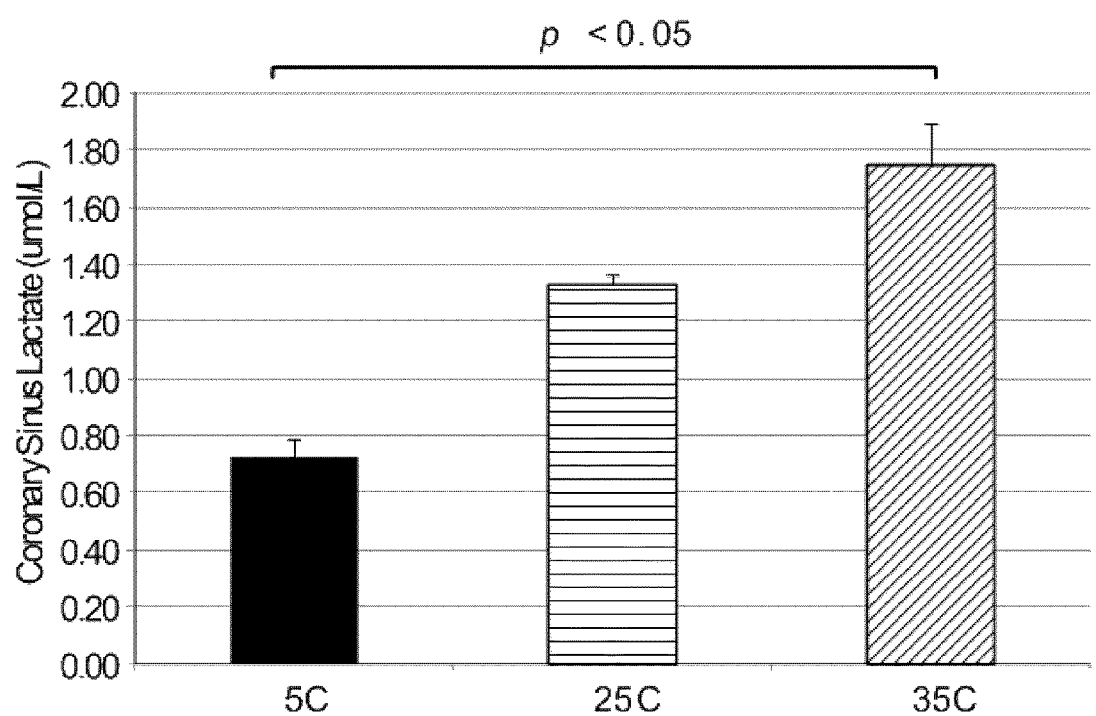
FIG. 5 is a chart showing the effects of temperature on coronary sinus lactate washout from harvested hearts, measured after the initial 3-minute reperfusion period.

FIG. 5 shows that the coronary sinus lactate dropped by more than 50% in hearts that received the chilled IE reperfusion treatment, and by about 25% in hearts that received the cooled IE reperfusion treatment, when compared to the coronary sinus lactate levels in the hearts receiving the normothermic IE reperfusion treatment.

Figure 6:
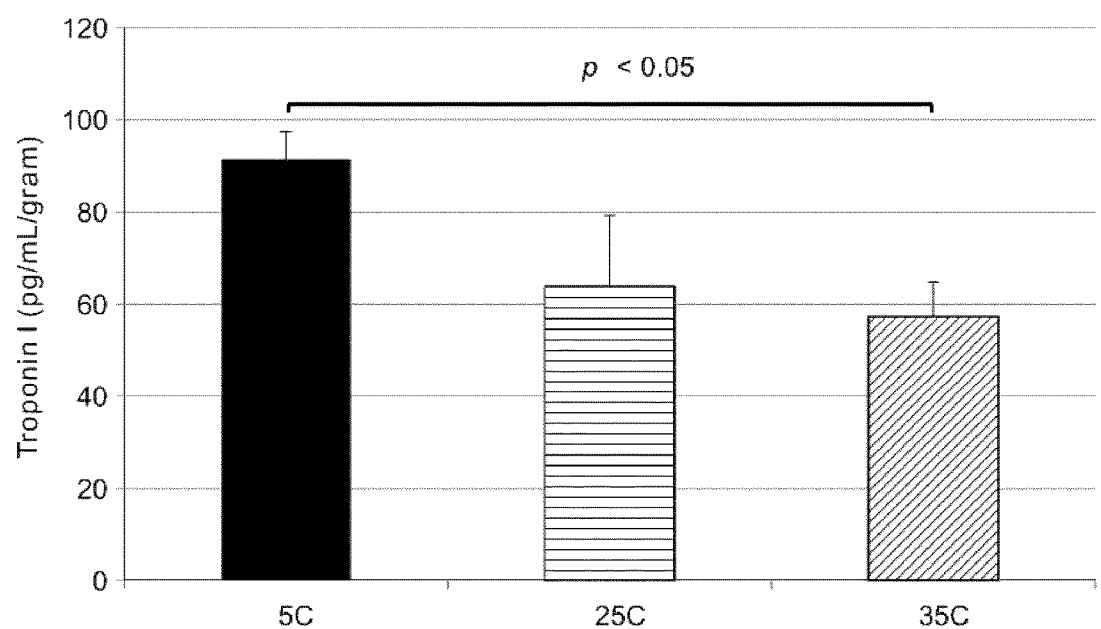
FIG. 6 is a chart showing the effects of temperature on the accumulations of troponin I (marker of myocardial injury) in the perfusate solutions after 5 hours of reperfusion of the harvested hearts.

FIG. 6 shows that levels of Troponin I (a marker for myocardial injury) increased as the temperature of the IE reperfusion temperature decreased, relative to the levels observed in hearts receiving the normothermic IE reperfusion treatment.

Figure 7:
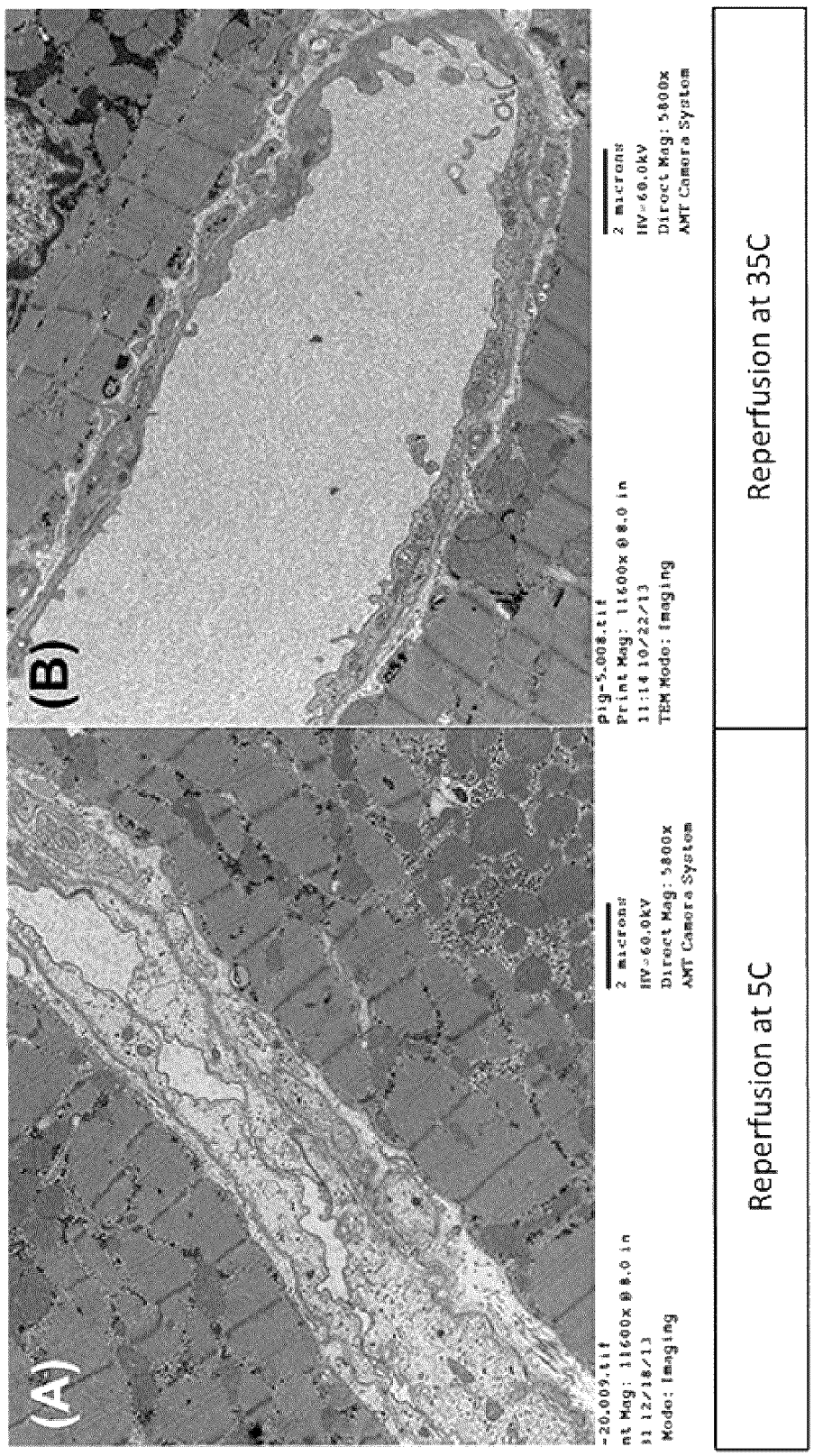

FIG. 7(A) is an electron micrograph showing a swollen endothelial cell in a capillary of a heart that received the chilled IE reperfusion treatment for 3 minutes, while FIG. 7(B) is an electron micrograph showing a typical normal-appearing endothelial cell in a capillary of a heart that received the normothermic IE reperfusion treatment for 3 minutes.

Figure 8:
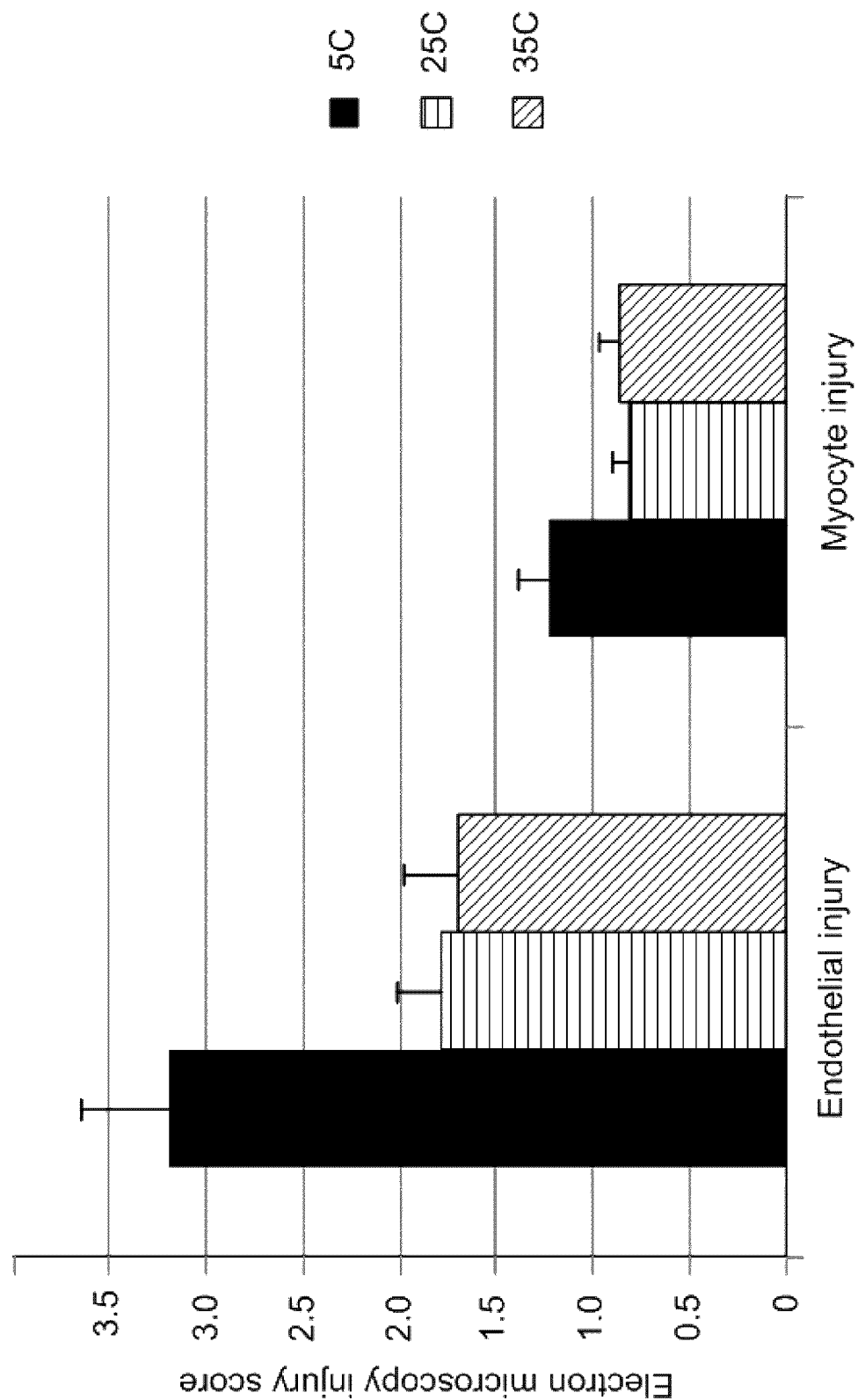
FIG. 8 is a micrograph showing the effects of reperfusion temperature on injuries to endothelial cells and myocytes in harvested hearts.

FIG. 8 is a chart comparing the scores of endothelial injury and myocyte injury from hearts receiving chilled IE reperfusion for three minutes and from hearts receiving normothermic IE reperfusion for three minutes.

Figure 9:
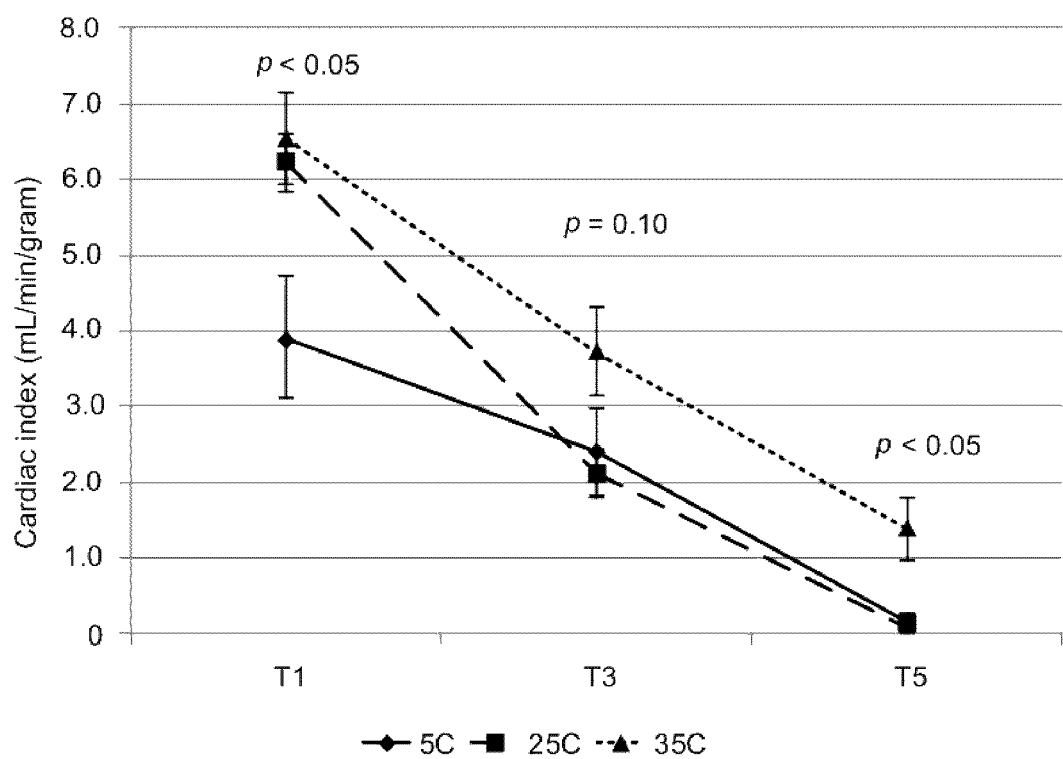
FIG. 9 is a chart showing the effects of temperature on the cardiac index of harvested hearts after 1 h, 2 h, and 3 h of reperfusion.

FIG. 9 is a chart showing the effects on cardiac indices of IE reperfusion with a cooled oxygenated cardioplegic composition and with a chilled oxygenated cardioplegic composition, with the effects of IP perfusion with a normothermic oxygenated cardioplegic composition.

Figure 10:
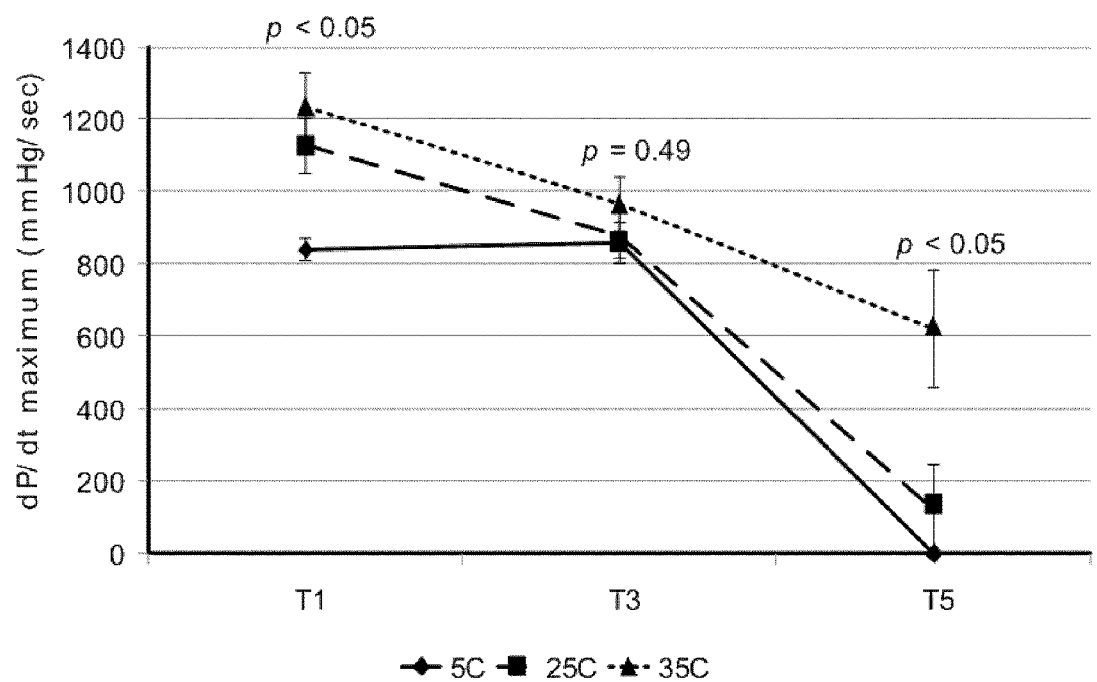
FIG. 10 is a chart showing the effects of temperature on the systolic function of harvested hearts after 1 h, 2 h, and 3 h of reperfusion.

FIG. 10 is a chart comparing the effects of the initial IE reperfusion temperatures on the subsequent systolic functioning of harvested hearts after 1 h, 2 h, and 3 h of resuscitation and perfusion of the hearts with the blood-STEEN solution mixture.

Figure 11:
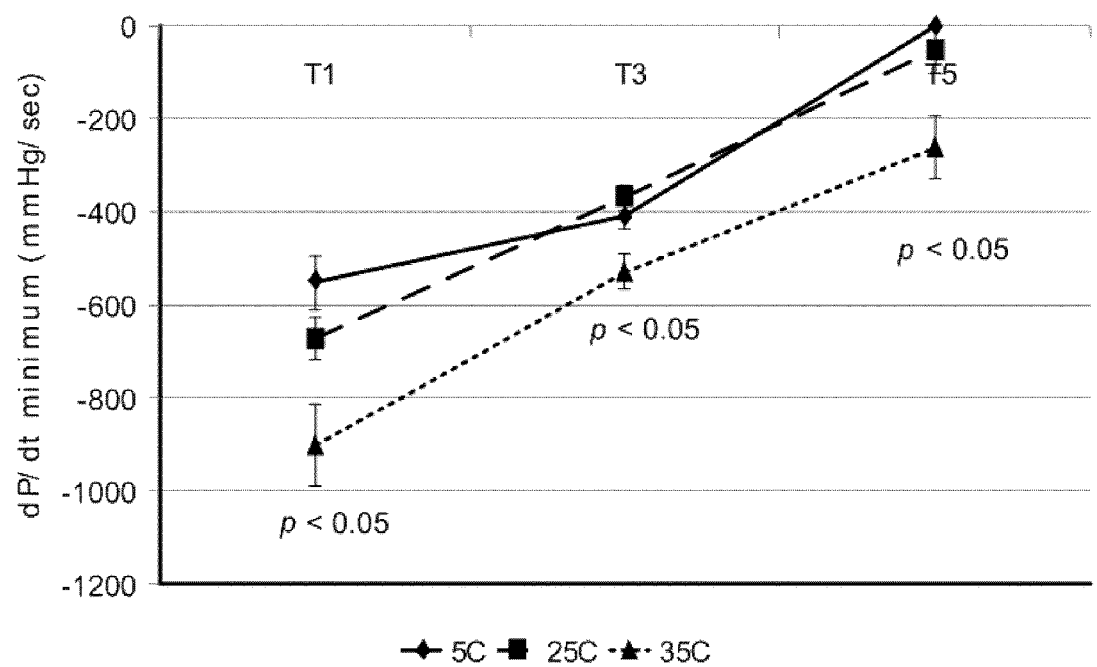
FIG. 11 is a chart showing the effects of temperature on the diastolic function of harvested hearts after 1 h, 2 h, and 3 h of reperfusion.

FIG. 11 is a chart comparing the effects of the initial IE reperfusion temperatures on the subsequent diastolic functioning of harvested hearts after 1 h, 2 h, and 3 h of resuscitation and perfusion of the hearts with the blood-STEEN solution mixture.

The data collected in this study demonstrate that the initial reperfusion conditions significantly impact the severity of post-harvest trauma to hearts removed from DCD donors, and the functional recovery of the reperfused hearts.

Example 2

Figure 12:
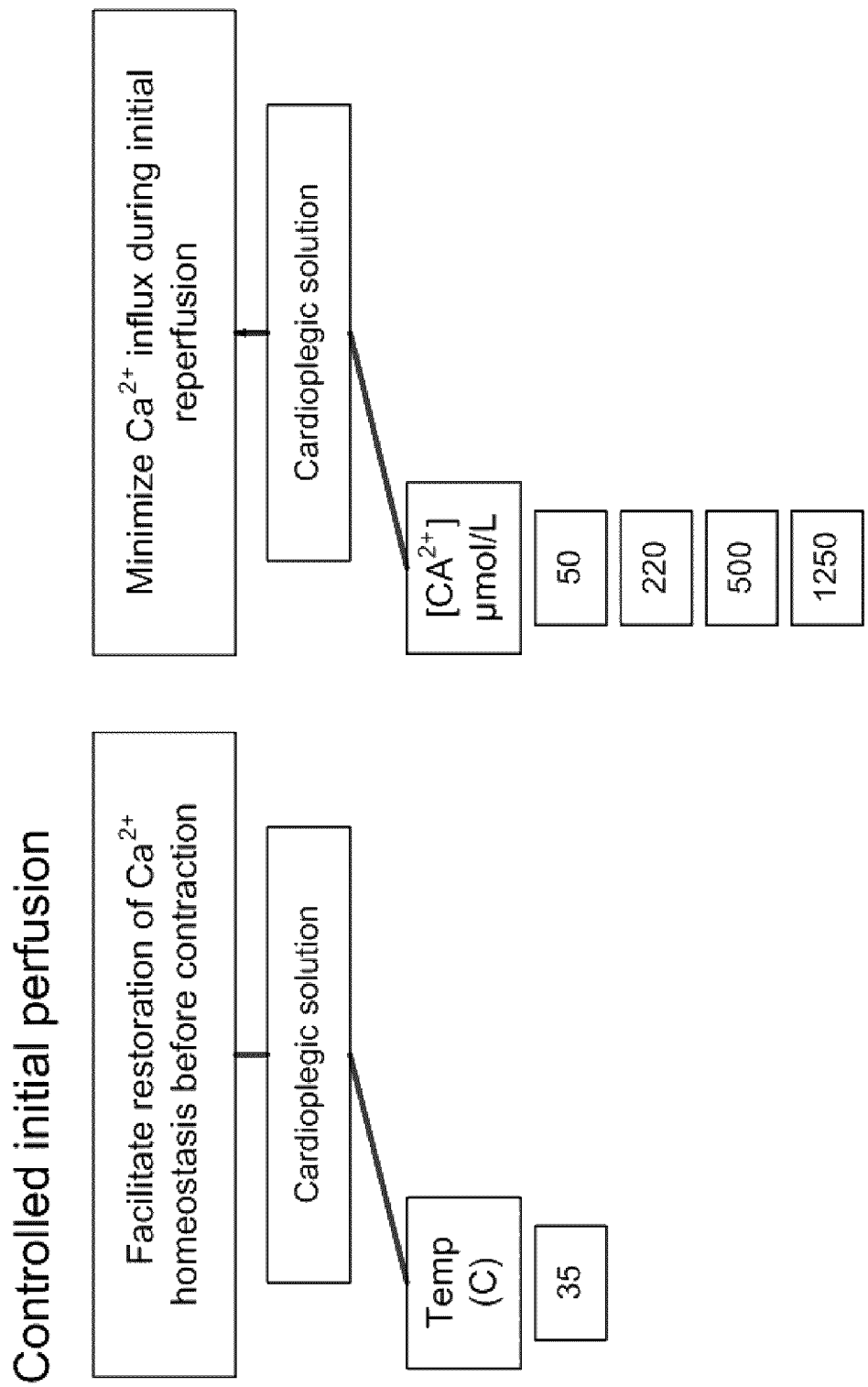
FIG. 12 is a schematic chart outlining the temperatures and $Ca^{2+}$ ion concentrations of the cardioplegic solutions used in Example 2.

The second study assessed the effects of reducing the $Ca^{2+}$ ion concentration in cardioplegic solutions to determine if lowering the $Ca^{2+}$ levels on the outside of myocytes would minimize the reverse mode functioning of the $Na^+/Ca^{2+}$ pump thereby reducing the accumulation of $Ca^{2+}$ ions within the myocytes. Accordingly, this study assessed the effects of 50 µmol/L, 220 µmol/L, 500 µmol/L, and 1250 µmol/L of $Ca^{2+}$ ions in the cardioplegic solutions (FIG. 12). All reperfusions were done at 35° C.

Figure 13:
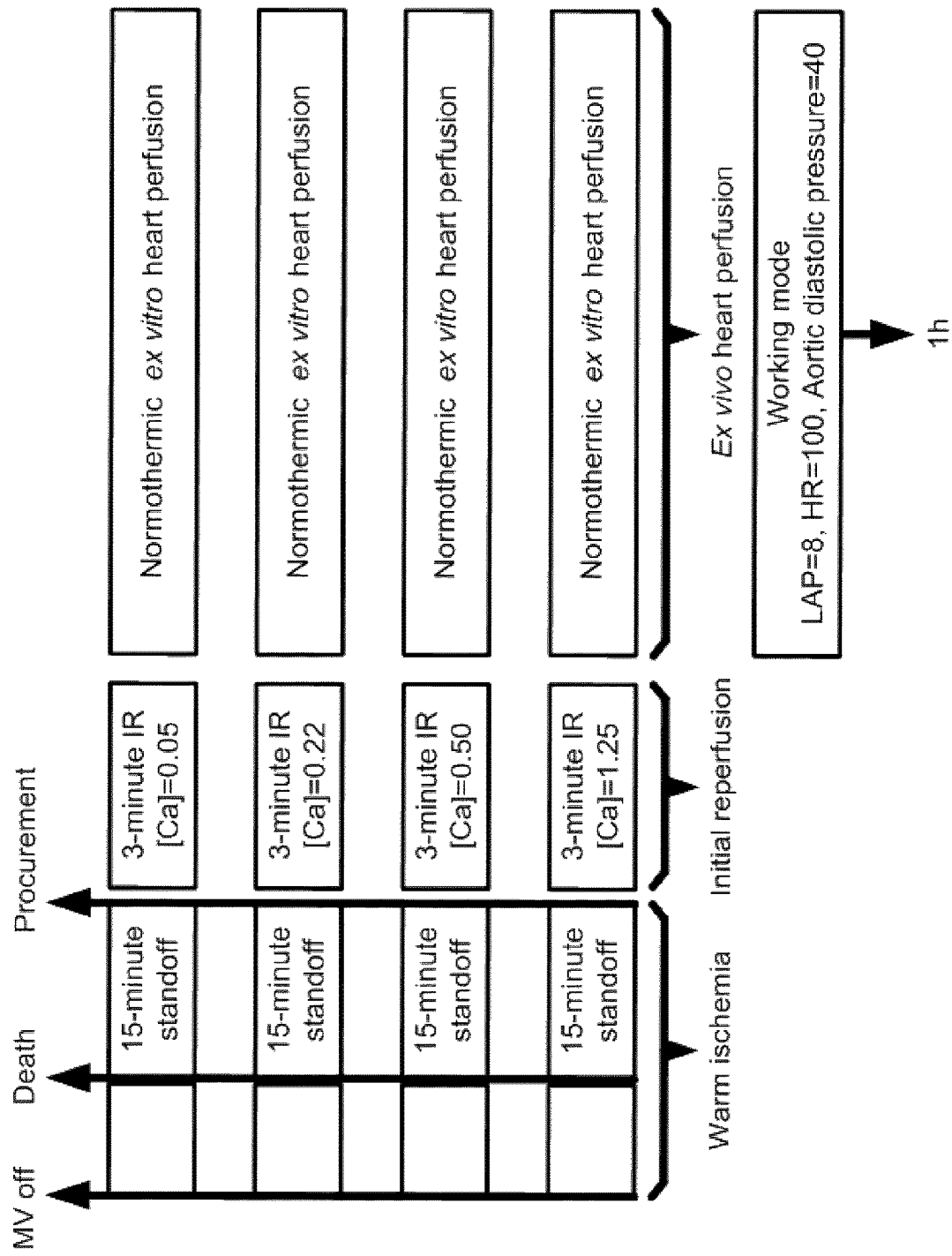
FIG. 13 is a schematic flowchart outlining the experimental protocols used in Example 2.

Twenty four pigs were separated into four groups and then euthanized following standard protocols and medical ethics procedures following the schematic flowchart shown in FIG. 13. Immediately after procurement of each heart was completed, each heart was installed into a Quest MPS®2 Myocardial Protection System. The harvested hearts from the first group of pigs were perfused for 3 minutes with the exemplary oxygenated cardioplegic composition containing 50 µmol/L $Ca^{2+}$ ions, that was warmed to 35° C. prior to commencing the reperfusion process. The harvested hearts from the second group of pigs were perfused for 3 minutes with the exemplary oxygenated cardioplegic composition containing 220 µmol/L $Ca^{2+}$ ions, that was warmed to 35° C. prior to commencing the reperfusion process. The harvested hearts from the third group of pigs were perfused for 3 minutes with the exemplary oxygenated cardioplegic composition containing 500 µmol/L $Ca^{2+}$ ions, that was warmed to 35° C. prior to commencing the reperfusion process. The harvested hearts from the fourth group of pigs were perfused for 3 minutes with the exemplary oxygenated cardioplegic composition containing 1,250 µmol/L $Ca^{2+}$ ions, that was warmed to 35° C. prior to commencing the reperfusion process.

The aortic perfusion pressure, coronary artery flow, and myocardial temperature were constantly monitored and recorded by the MPS®² apparatus during the 3-minute initial reperfusion period. Blood gas samples were measured at 0, 30, 60, 120, and 180 seconds of the initial reperfusion period to collect data pertaining to changes occurring the partial pressure of $O_2$ ($PaO_2$), partial pressure of $CO_2$ ($PaCO_2$), pH levels, electrolyte levels, lactate levels among others.

After the initial 3-minute reperfusion period was completed. Each heart was removed from the Quest MPS®2 apparatus and transferred into an ex vivo heart perfusion (EVHP) apparatus where it was perfused with a constantly flowing supply of a blood-STEEN solution mixture (Hb 45 g/L; XVIVO Perfusion Inc., Englewood, Colo., USA) wherein its systolic function was restored and maintained in a Landorff mode at a normothermic temperature of 35° C. for 1 hour. The aortic pressure and heart rate were constantly monitored and processed using the LABCHART® software. At 1 h of perfusion with the blood-STEEN solution mixture in the EVHP apparatus, each heart was transitioned from the Langendorff mode to a working mode by bringing the left atrial pressure from 0 to 8 mmHg and pacing the heart at 100 bpm. Cardiac output, coronary blood flow, aortic root, and coronary sinus blood gases were measured, and cardiac function was assessed with a pressure-volume loop catheter. After these measurements were completed, each heart was immediately returned to the Langendorff mode.

Figure 14:
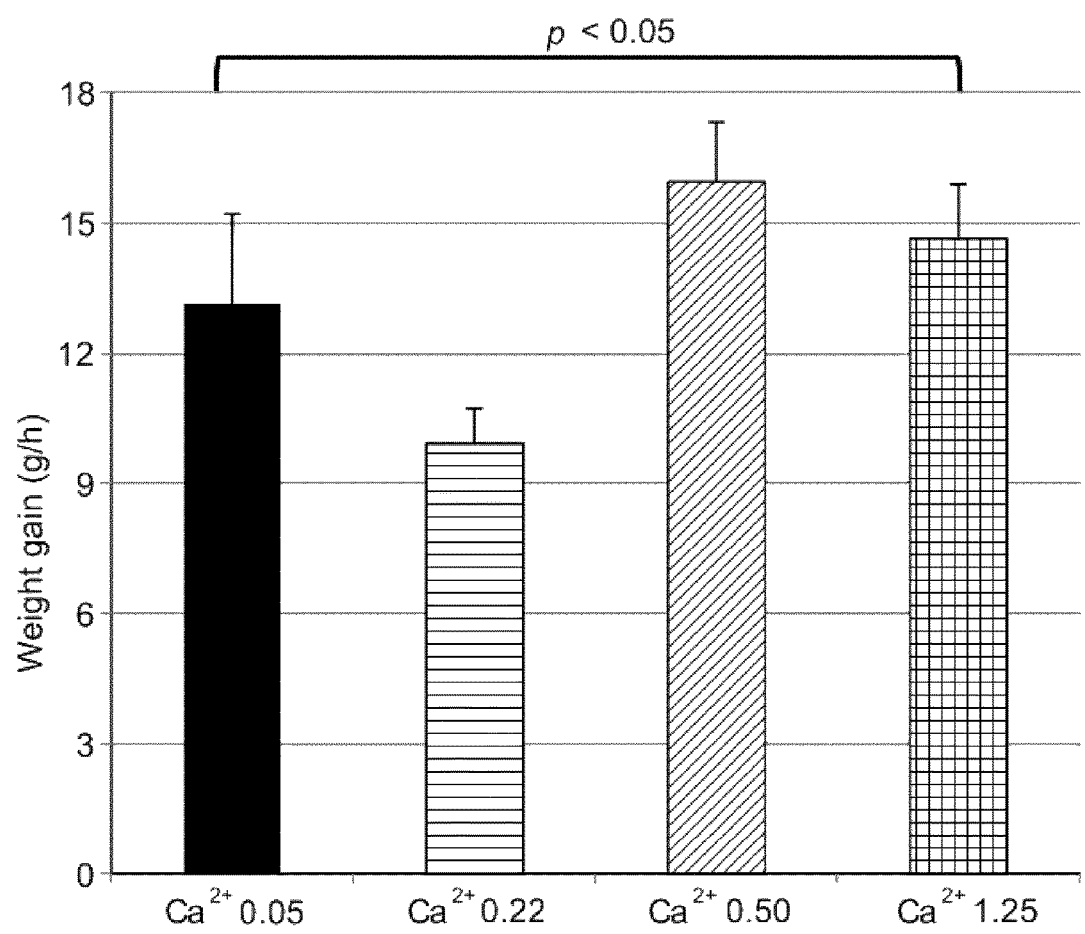
FIG. 14 is a chart showing the effects of increasing $Ca^{2+}$ ion concentrations on weight gain in reperfused harvested hearts.

FIG. 14 shows that the hearts initially reperfused at 35° C. with the exemplary oxygenated cardioplegic composition containing 220 µmol/L $Ca^{2+}$ ions developed significantly less myocardial edema than the hearts reperfused with oxygenated cardioplegic compositions containing one of the other three $Ca^{2+}$ ion concentrations.

Figure 15:
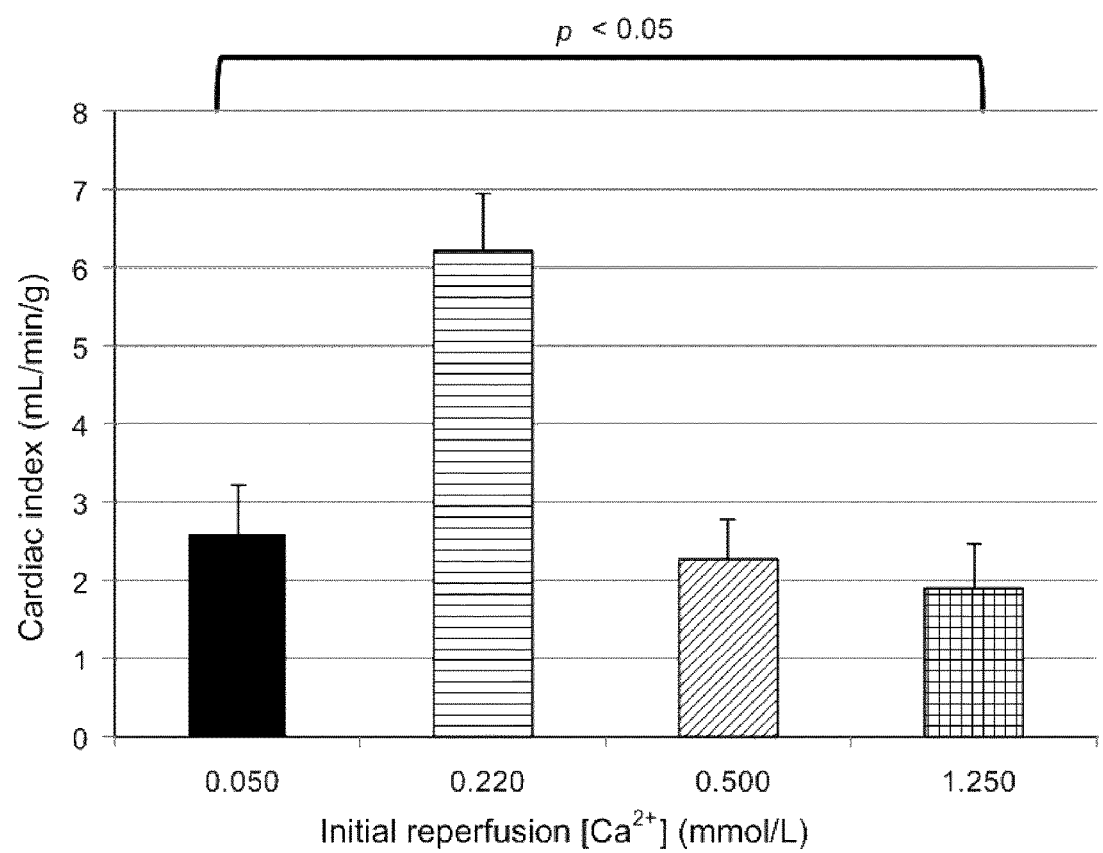
FIG. 15 is a chart showing the effects of increasing $Ca^{2+}$ ion concentrations on the cardiac output of harvested hearts after 1 h of ex vivo reperfusion.

FIG. 15 shows that the cardiac output (indexed for heart weight) of reperfused hearts improved as the $Ca^{2+}$ ion concentration in the oxygenated cardioplegic compositions was reduced from 1,250 µmol/L to 500 µmol/L to 220 µmol/L. However, the cardiac output of hearts reperfused with an oxygenated cardioplegic composition containing 50 µmol/L $Ca^{2+}$ ions was very poor, presumably due to the "calcium paradox" wherein ischemia alone, through ATP depletion, can cause an increase in cytoplasmic calcium concentrations.

Figure 16:
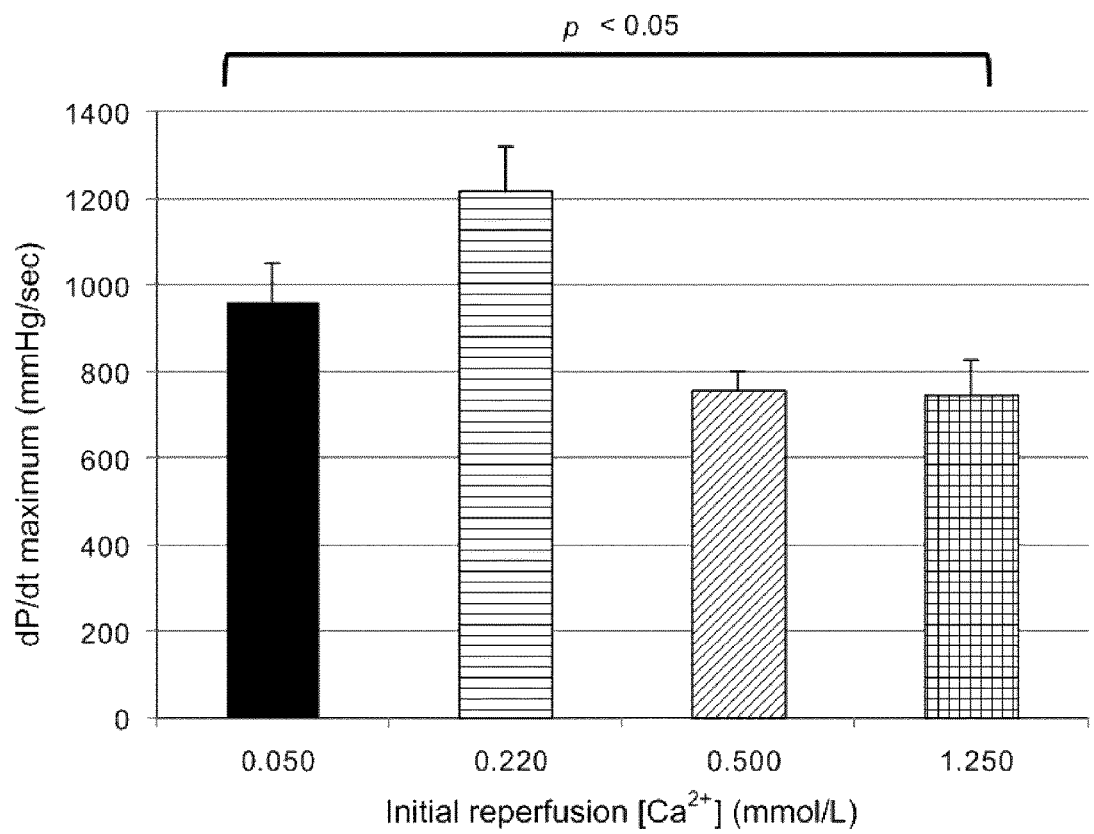
FIG. 16 is a chart showing the effects of increasing $Ca^{2+}$ ion concentrations on the contractility of the left ventricle during systole in harvested hearts after 1 h of ex vivo reperfusion.

FIG. 16 shows that the contractility of the left ventricle (as measured by dP/dt max) during systole in reperfused hearts improved as the $Ca^{2+}$ ion concentration in the oxygenated cardioplegic compositions was reduced from 1,250 µmol/L to 500 µmol/L to 220 µmol/L. However, contractility of the left ventricle in hearts reperfused with the oxygenated cardioplegic composition containing 50 µmol/L $Ca^{2+}$ ions was very poor, also presumably due to the calcium paradox.

Figure 17:
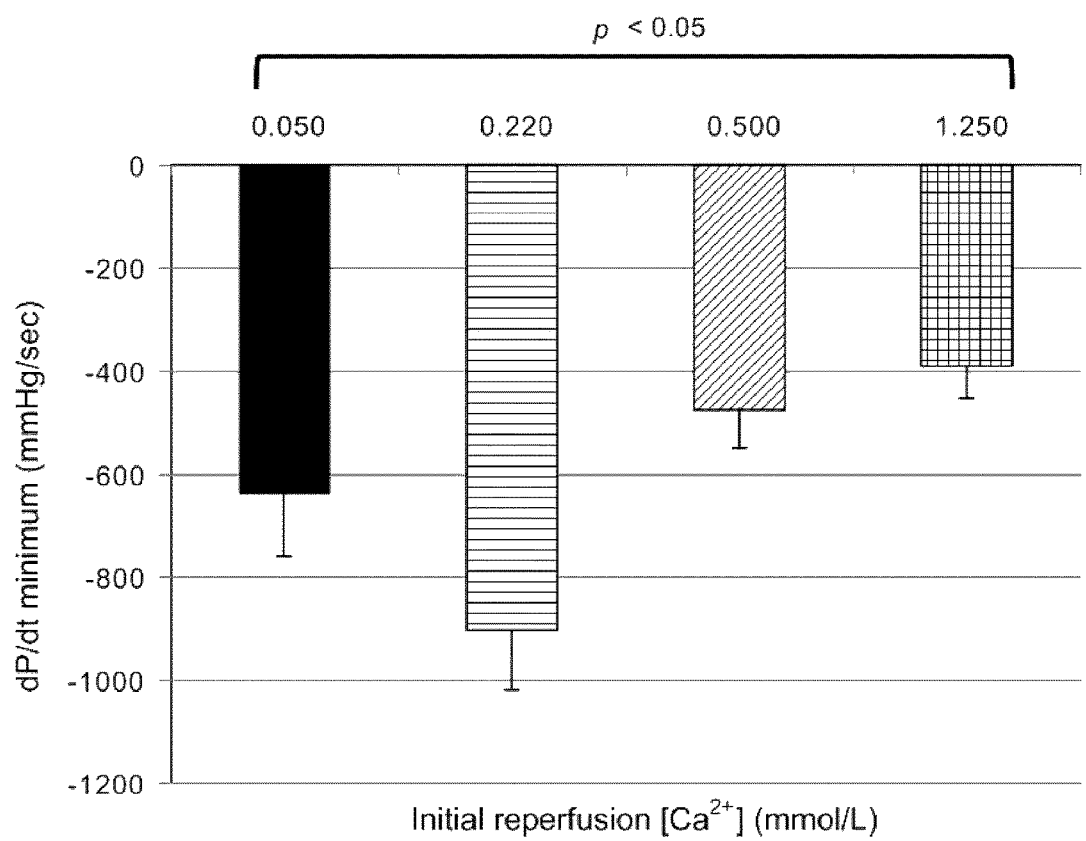
FIG. 17 is a chart showing the effects of increasing $Ca^{2+}$ ion concentrations on relaxation of the left ventricle during diastole in harvested hearts after 1 h of ex vivo reperfusion.

FIG. 17 shows that the relaxation of the left ventricle (as measured by dP/dt min) during diastole in reperfused hearts improved as the $Ca^{2+}$ ion concentration in the oxygenated cardioplegic compositions was reduced from 1,250 µmol/L to 500 µmol/L to 220 µmol/L. However, relaxation of the left ventricle in hearts reperfused with the oxygenated cardioplegic composition containing 50 µmol/L $Ca^{2+}$ ions was very poor, also presumably due to the calcium paradox.

The data collected during this study demonstrate that initial reperfusion Of harvested hearts with hypocalcemic oxygenated cardioplegic compositions at 35° C. significantly improved myocardial functional recovery. The best performance in this study was with a $Ca^{2+}$ ion concentration. However, it appears that reducing the $Ca^{2+}$ ion concentration too low, e.g., to 50 µmol/L, may have detrimental effects.

Example 3

Figure 18:
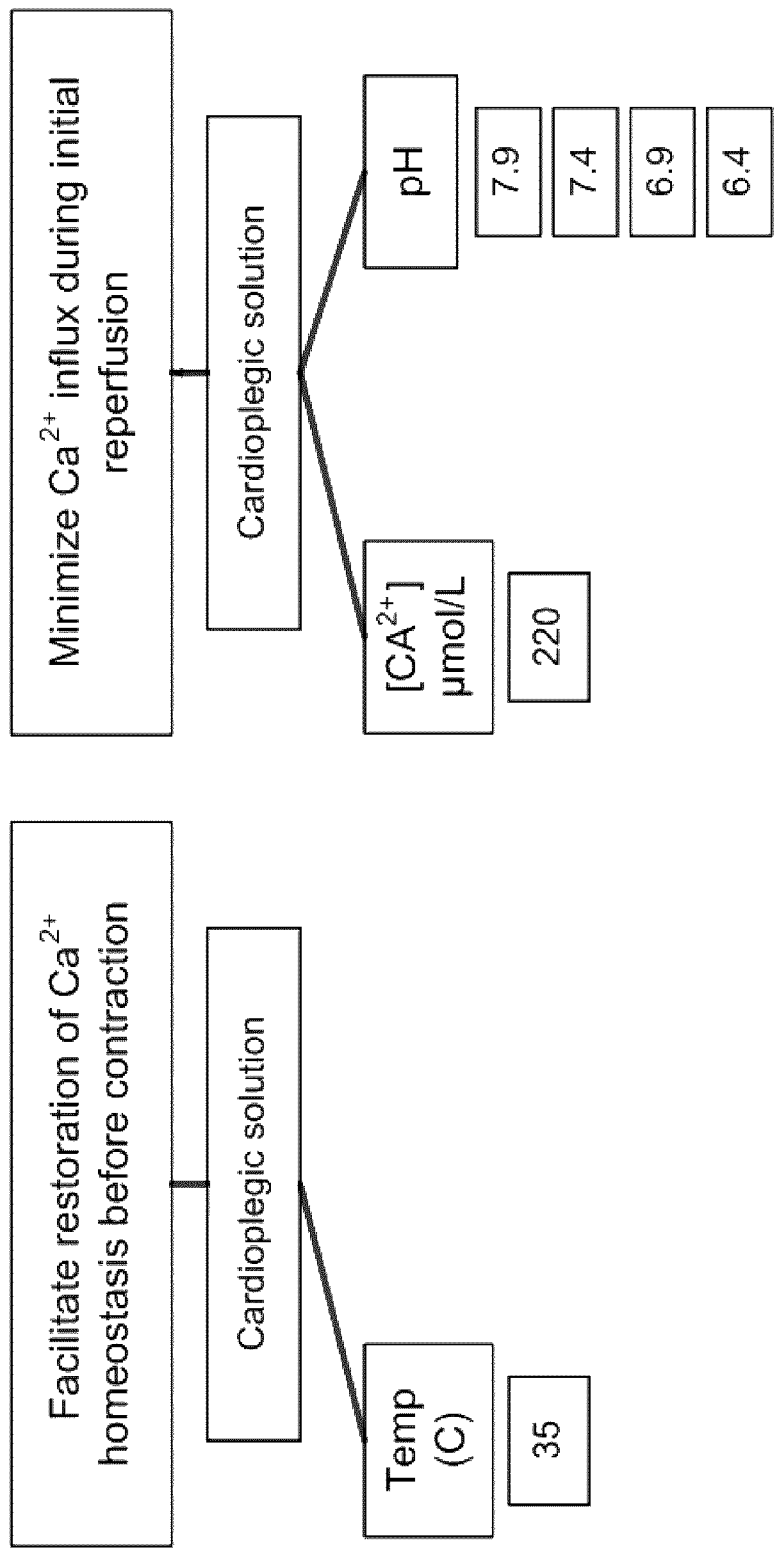
FIG. 18 is a schematic chart outlining the temperatures, $Ca^{2+}$ ion concentrations, and pHs of the cardioplegic solutions used in Example 3.

The next study assessed if there were potential incremental benefits to acidification of a hypocalcemic oxygenated cardioplegic composition. Accordingly, this study assessed the effects of adjusting the pH of an exemplary hypocalcemic oxygenated cardioplegic composition from 7.9 to 7.4 to 6.9 to 6.4. The cardioplegic solution contained 220 µmol/L of $Ca^{2+}$ ions in the cardioplegic solutions and all reperfusions were done at 35° C. (FIG. 18).

Figure 19:
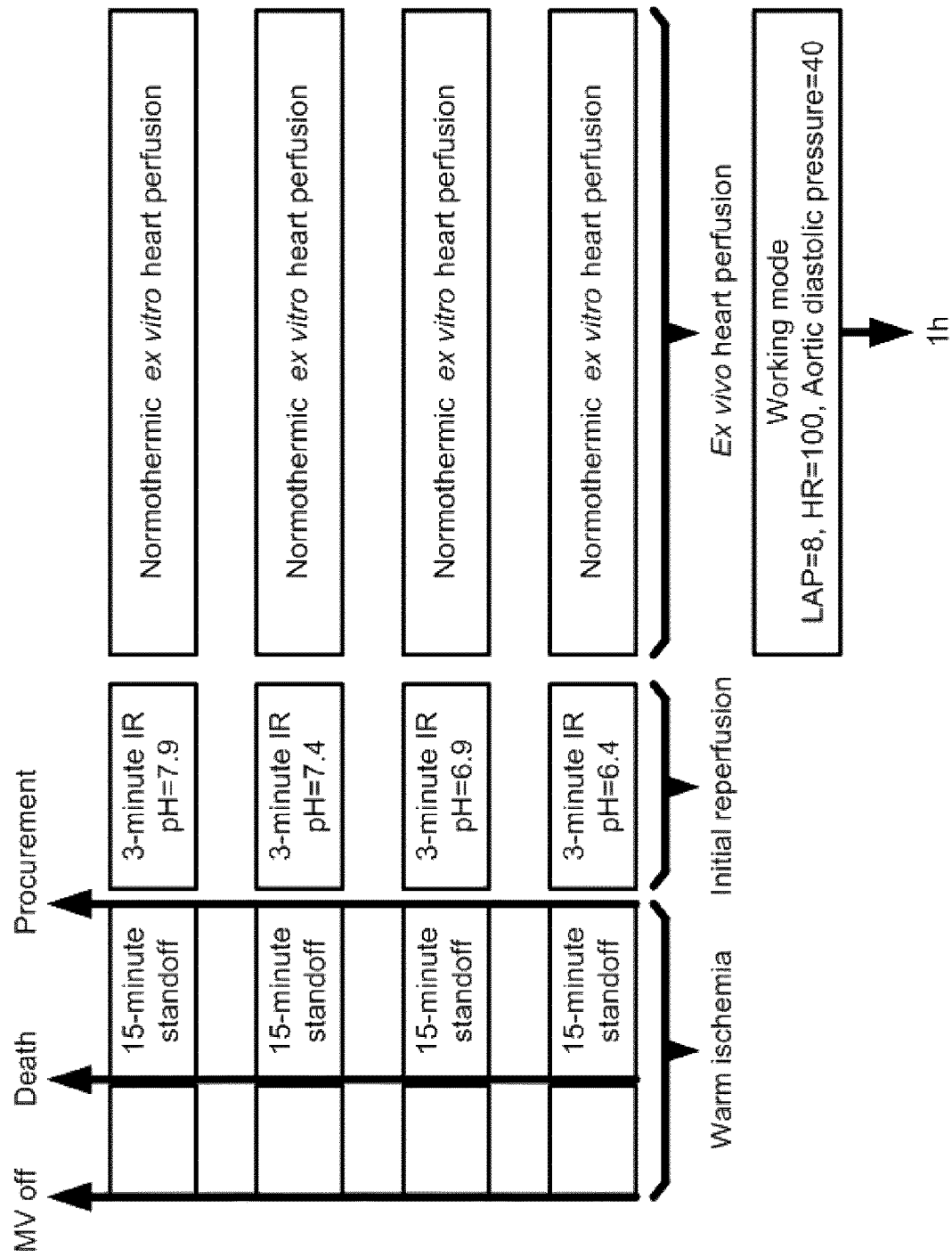
FIG. 19 is a schematic flowchart outlining the experimental protocols used in Example 3.

Twenty four pigs were separated into four groups and then euthanized following standard protocols and medical ethics procedures following the schematic flowchart shown in FIG. 19. Immediately after procurement of each heart was completed, each heart was installed into a Quest MPS®2 Myocardial Protection System. The harvested hearts from the first group of pigs were perfused for 3 minutes with the exemplary hypocalcemic oxygenated cardioplegic composition with a pH of 7.9, that was warmed to 35° C. prior to commencing the reperfusion process. The harvested hearts from the second group of pigs were perfused for 3 minutes with the exemplary hypocalcemic oxygenated cardioplegic composition adjusted to a pH of 7.4, that was warmed to 35° C. prior to commencing the reperfusion process. The harvested hearts from the third group of pigs were perfused for 3 minutes with the exemplary hypocalcemic oxygenated cardioplegic composition adjusted to a pH of 6.9, that was warmed to 35° C. prior to commencing the reperfusion process. The harvested hearts from the fourth group of pigs were perfused for 3 minutes with the exemplary hypocalcemic oxygenated cardioplegic composition adjusted to a pH of 6.4, that was warmed to 35° C. prior to commencing the reperfusion process.

The aortic perfusion pressure, coronary artery flow, and myocardial temperature were constantly monitored and recorded by the MPS®2 apparatus during the 3-minute initial reperfusion period. Blood gas samples were measured at 0, 30, 60, 120, and 180 seconds of the initial reperfusion period to collect data pertaining to changes occurring the partial pressure of $O_2$ ($PaO_2$), partial pressure of $CO_2$ ($PaCO_2$), pH levels, electrolyte levels, lactate levels among others.

After the initial 3-minute reperfusion period was completed. Each heart was removed from the Quest MPS®2 apparatus and transferred into an ex vivo heart perfusion (EVHP) apparatus where it was perfused with a constantly flowing supply of a blood-STEEN solution mixture (Hb 45 g/L; XVIVO Perfusion Inc., Englewood, Colo., USA) wherein its systolic function was restored and maintained in a Landorff mode at a normothermic temperature of 35° C. for 1 hour. The aortic pressure and heart rate were constantly monitored and processed using the LABCHART® software. At 1 h of perfusion with the blood-STEEN solution mixture in the EVHP apparatus, each heart was transitioned from the Langendorff mode to a working mode by bringing the left atrial pressure from 0 to 8 mmHg and pacing the heart at 100 bpm. Cardiac output, coronary blood flow, aortic root, and coronary sinus blood gases were measured, and cardiac function was assessed with a pressure-volume loop catheter. After these measurements were completed, each heart was immediately returned to the Langendorff mode.

Figure 20:
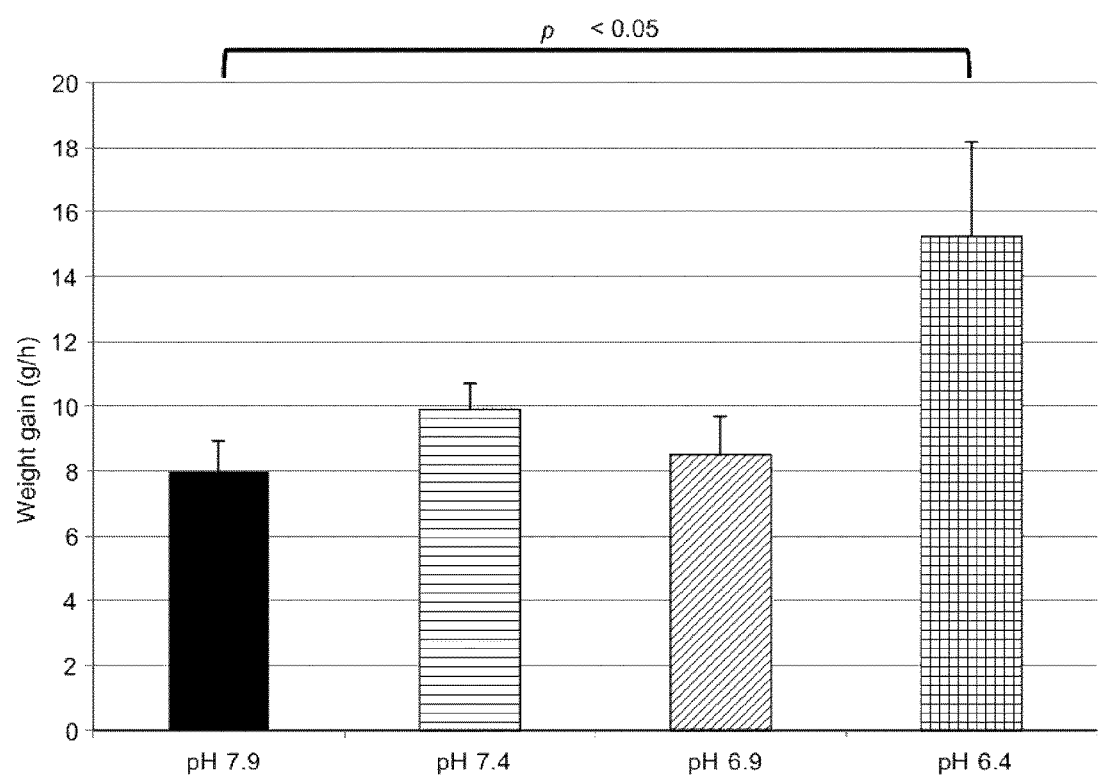
FIG. 20 is a chart showing the effects of decreasing the pH in cardioplegic solutions on weight gain in reperfused harvested hearts.

FIG. 20 shows that the hearts initially reperfused at 35° C. with the exemplary hypocalcemic oxygenated cardioplegic compositions that was mildly acidified (i.e., pH 6.4) exhibited more myocardial edema than those that were reperfused with the alkalotic (i.e., pHs 7.9, 7.4, 6.9) hypocalcemic oxygenated cardioplegic compositions.

Figure 21:
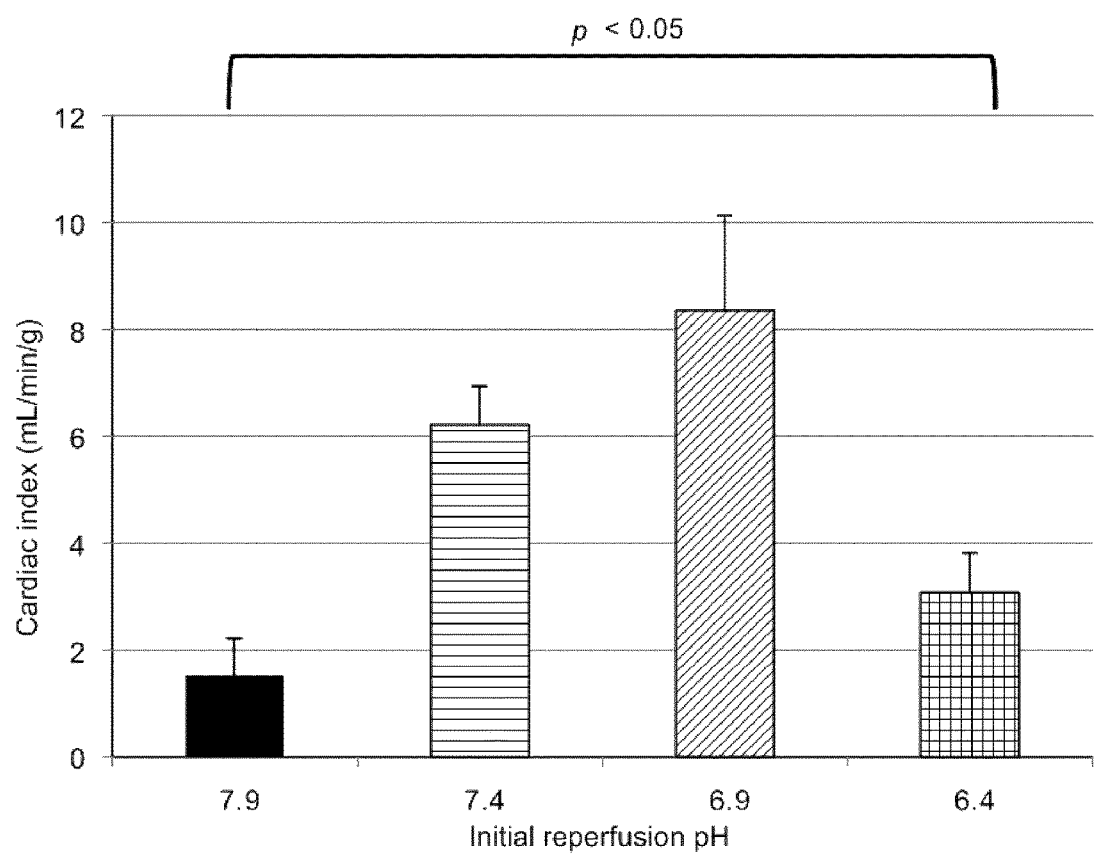
FIG. 21 is a chart showing the effects of decreasing the pHs on the cardiac output of harvested hearts after 1 h of ex vivo reperfusion.

FIG. 21 shows that the cardiac outputs (indexed for heart weight) of reperfused hearts in a slightly acidified hypocalcemic oxygenated cardioplegic composition (i.e., pH 6.9) and a slightly alkalotic hypocalcemic oxygenated cardioplegic composition (i.e., pH 7.4) were significantly better that the cardiac outputs of hearts reperfused in hypocalcemic oxygenated cardioplegic compositions adjusted to pH 7.9 or 6.4.

Figure 22:
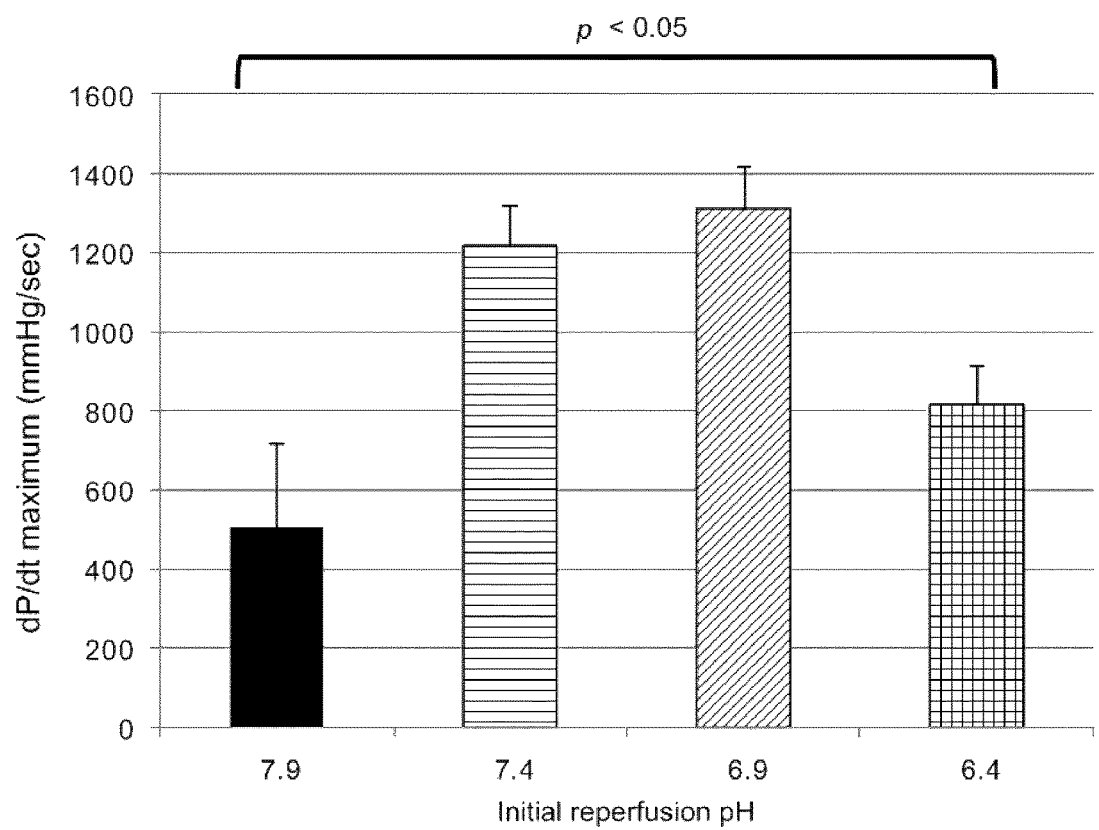
FIG. 22 is a chart showing the effects of decreasing the pHs on the contractility of the left ventricle during systole in harvested hearts after 1 h of ex vivo reperfusion.

FIG. 22 shows that the contractility of the left ventricle (as measured by dP/dt max) during systole in reperfused hearts in a slightly acidified hypocalcemic oxygenated cardioplegic composition (i.e., pH 6.9) and a slightly alkalotic hypocalcemic oxygenated cardioplegic composition (i.e., pH 7.4) were significantly better than the left ventricle contractility in hearts reperfused in hypocalcemic oxygenated cardioplegic compositions adjusted to pH 7.9 or 6.4.

Figure 23:
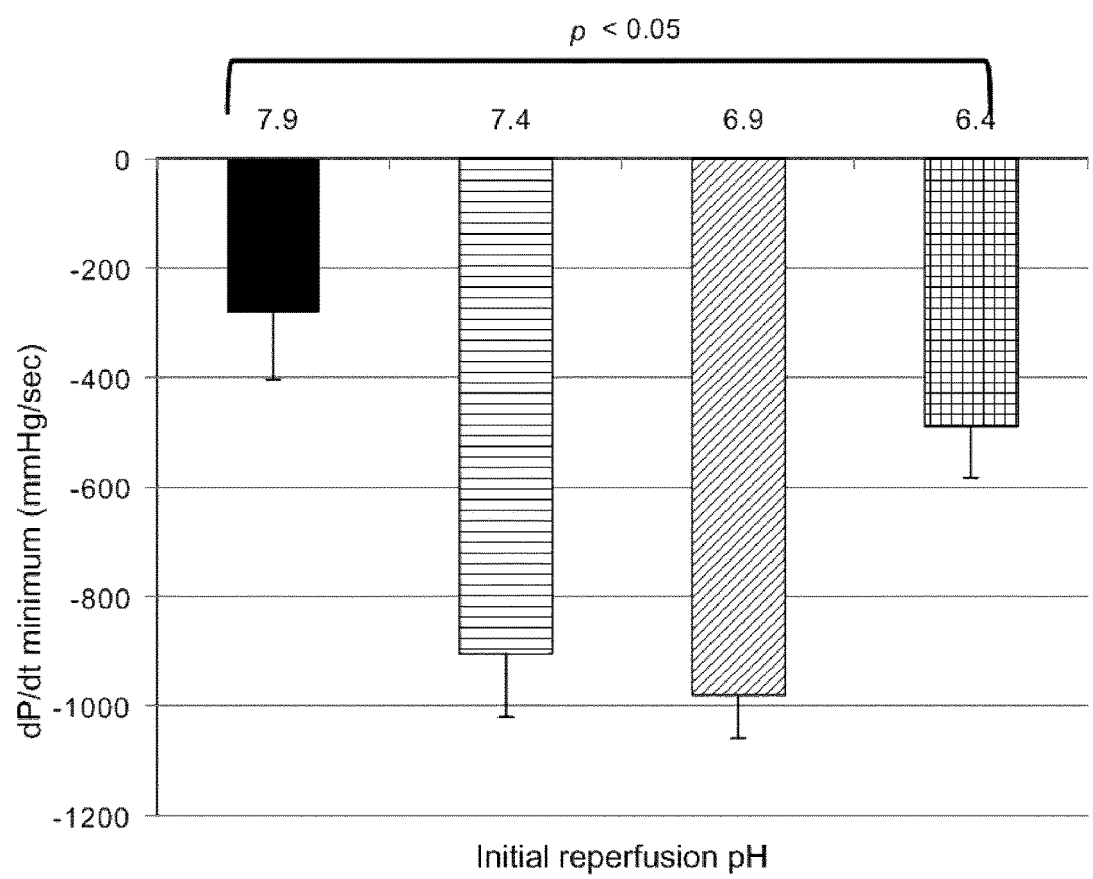
FIG. 23 is a chart showing the effects of decreasing the pHs on relaxation of the left ventricle during diastole in harvested hearts after 1 h of ex vivo reperfusion.

FIG. 23 shows that the relaxation of the left ventricle (as measured by dP/dt min) during diastole in reperfused hearts in a slightly acidified hypocalcemic oxygenated cardioplegic composition (i.e., pH 6.9) and a slightly alkalotic hypocalcemic oxygenated cardioplegic composition (i.e., pH 7.4) were significantly better than the left ventricle relaxation in hearts reperfused in hypocalcemic oxygenated cardioplegic compositions adjusted to pH 7.9 or 6.4.

The data collected during this study demonstrate that initial alkalotic reperfusion is detrimental and significant acidosis (e.g., pH less than 6.5) as also detrimental. However, it appears that mild acidosis (e.g. pH of 6.6 to 6.9) is beneficial.

Example 4

Part 1

Figure 24:
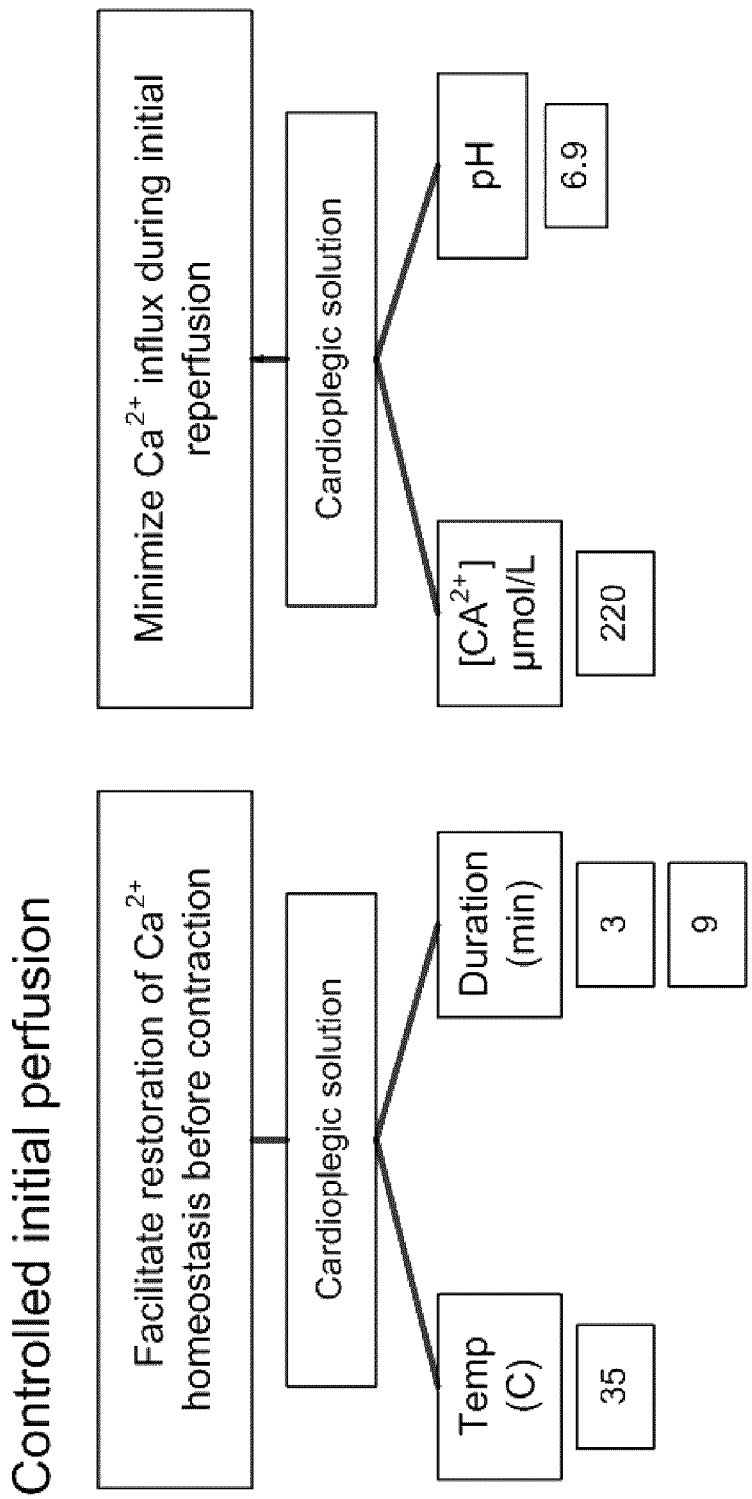
FIG. 24 is a schematic chart outlining the temperatures, $Ca^{2+}$ ion concentrations, and pHs of the cardioplegic solutions, and the duration of reperfusion times used in Example 4.

The next study assessed if there were potential incremental benefits to increasing the duration of reperfusion of harvested donor hearts with a mildly acidified hypocalcemic oxygenated cardioplegic composition. Accordingly, this study assessed the effects of 3 min or 9 min reperfusion with an exemplary mildly acided (pH 6.9) hypocalcemic (220 μmol/L $Ca^{2+}$) oxygenated cardioplegic solution at 35° C. (FIG. 24). The cardioplegic solution for Part 1 of this study contained 400 μmol/L adenosine and 500 μmol/L lidocaine.

Figure 25:
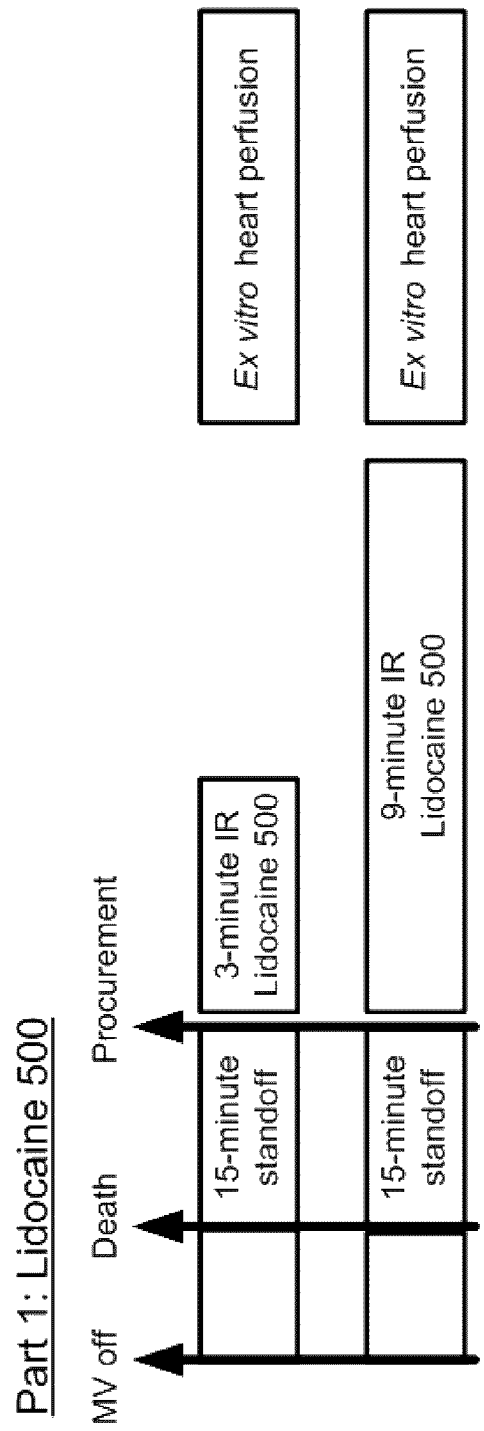
FIG. 25 is a schematic flowchart outlining the experimental protocols used in Example 4, Part 1.

Twelve pigs were separated into two groups and then euthanized following standard protocols and medical ethics procedures following the schematic flowchart shown in FIG. 25. Immediately after procurement of each heart was completed, each heart was installed into a Quest MPS®2 Myocardial Protection System. The harvested hearts from the first group of pigs were perfused for 3 minutes with the exemplary mildly acidic hypocalcemic oxygenated cardioplegic composition warmed to 35° C. prior to commencing the reperfusion process for 3 min. The harvested hearts from the second group of pigs were perfused for 9 minutes with the exemplary mildly acidic hypocalcemic oxygenated cardioplegic composition that was warmed to 35° C. prior to commencing the reperfusion process.

The aortic perfusion pressure, coronary artery flow, and myocardial temperature were constantly monitored and recorded by the MPS®2 apparatus during the 3-minute initial reperfusion period. Blood gas samples were measured at 0, 30, 60, 120, and 180 seconds of the initial reperfusion period to collect data pertaining to changes occurring the partial pressure of $O_2$ ($PaO_2$), partial pressure of $CO_2$ ($PaCO_2$), pH levels, electrolyte levels, lactate levels among others.

After the initial 3-minute reperfusion period or the initial 9-minute reperfusion period was completed, each heart was removed from the Quest MPS®2 apparatus and transferred into an ex vivo heart perfusion (EVHP) apparatus where it was perfused with a constantly flowing supply of a blood-STEEN solution mixture (Hb 45 g/L; XVIVO Perfusion Inc., Englewood, Colo., USA) wherein its systolic function was restored and maintained in a Landorff mode at a normothermic temperature of 35° C. for 1 h, 3 h, and 5 h. The aortic pressure and heart rate were constantly monitored and processed using the LABCHART® software. At 1 h of perfusion with the blood-STEEN solution mixture in the EVHP apparatus, each heart was transitioned from the Langendorff mode to a working mode by bringing the left atrial pressure from 0 to 8 mmHg and pacing the heart at 100 bpm. Cardiac output, coronary blood flow, aortic root, and coronary sinus blood gases were measured, and cardiac function was assessed with a pressure-volume loop catheter. After these measurements were completed, each heart was immediately returned to the Langendorff mode for an additional 2 h, after which the measurements were repeated (i.e., 3 h after removal from reperfusion). After these measurements were completed, each heart was immediately returned to the Langendorff mode for an additional 2 h, after which the measurements were repeated (i.e., 5 h after removal from reperfusion).

Figure 26:
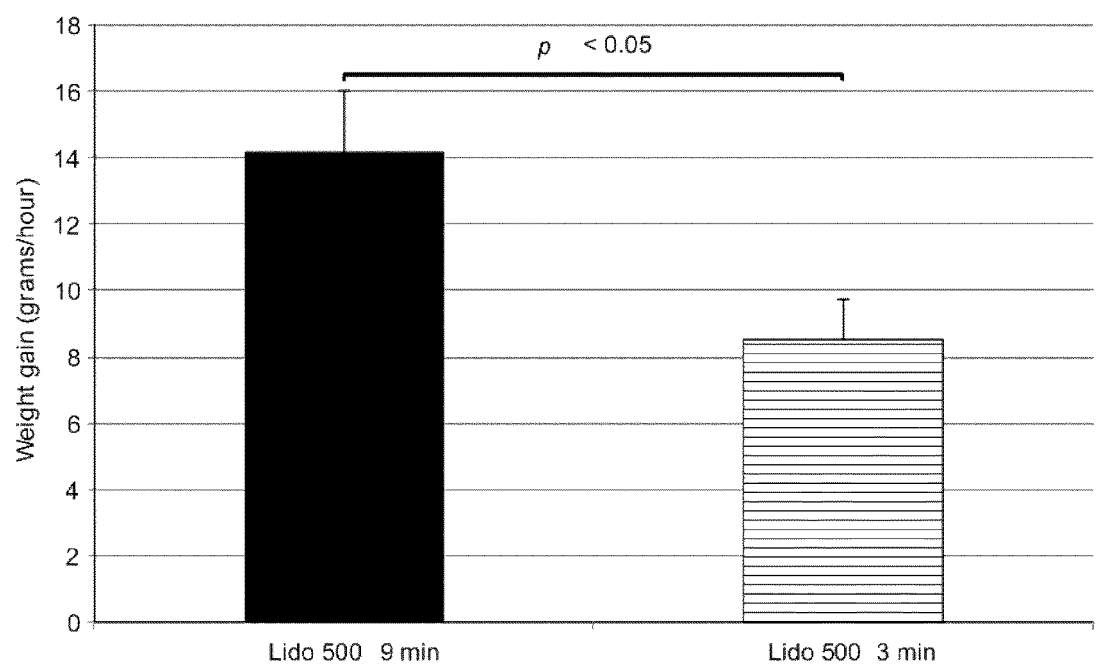
FIG. 26 is a chart showing the effects of duration of initial reperfusion on weight gain in reperfused harvested hearts.

FIG. 26 shows that the hearts initially reperfused for 9 min with the exemplary mildly acidic hypocalcemic oxygenated cardioplegic composition exhibited more myocardial edema than those that were reperfused for only 3 min.

Figure 27:
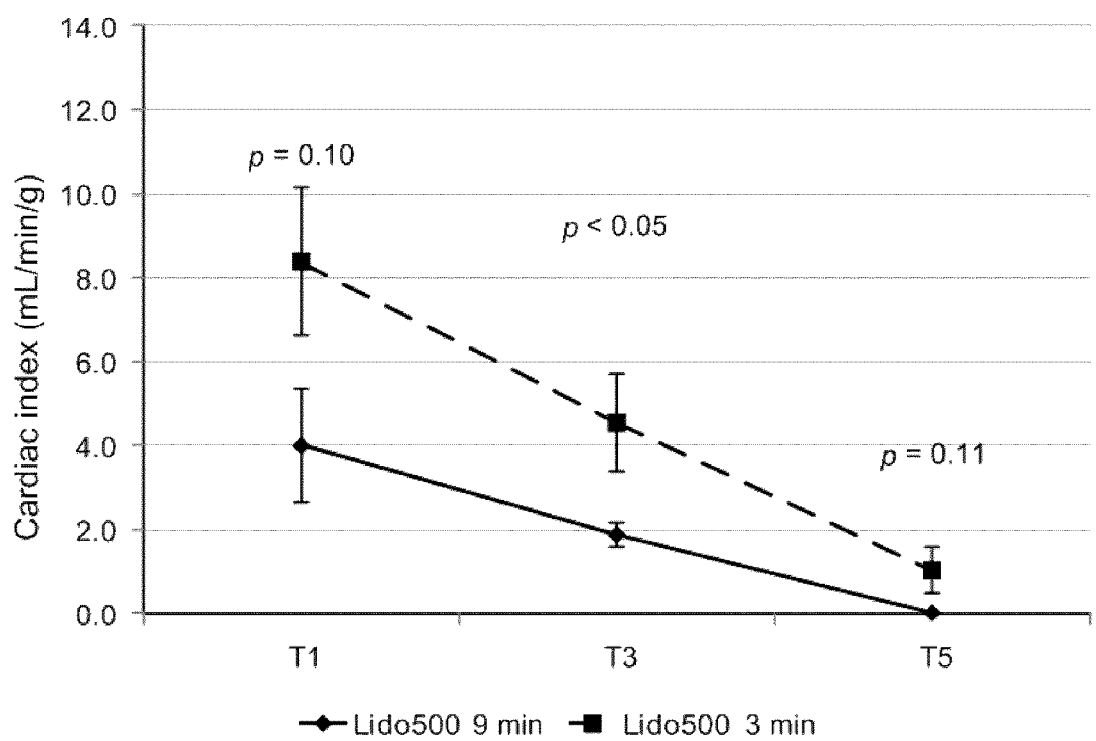
FIG. 27 is a chart showing the effects of duration of initial reperfusion on myocardial function of harvested hearts.

FIG. 27 shows that the hearts initially reperfused for 9 minutes trended toward worsening function as ex vivo heart perfusion proceeded from 1 h to 3 h to 5 h.

These data suggest that the cardioplegic composition may contain one or more toxic constituents.

Part 2

Figure 28:
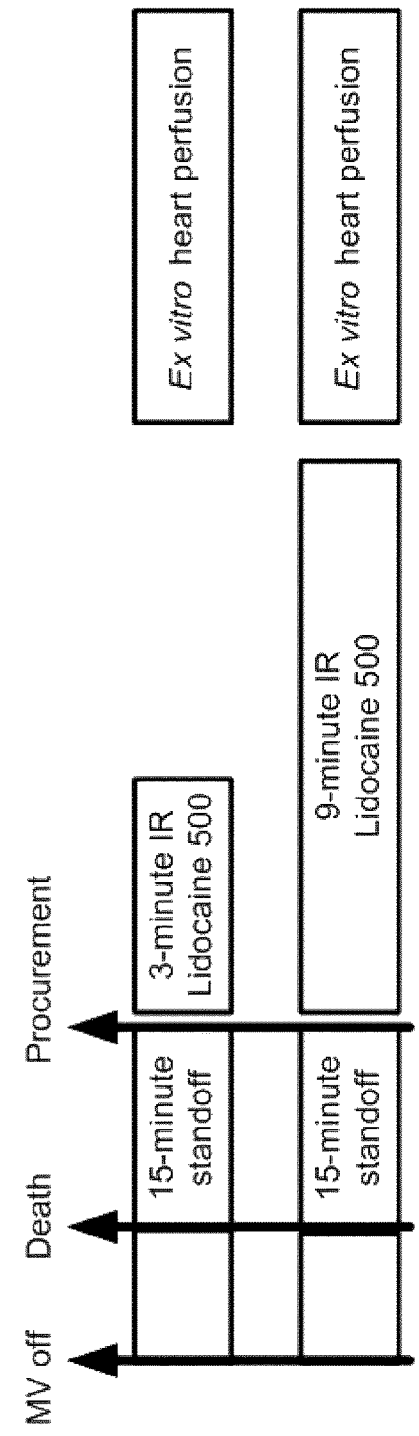
FIG. 28 is a schematic flowchart outlining the experimental protocols used in Example 4, Part 2.
Figure 28:
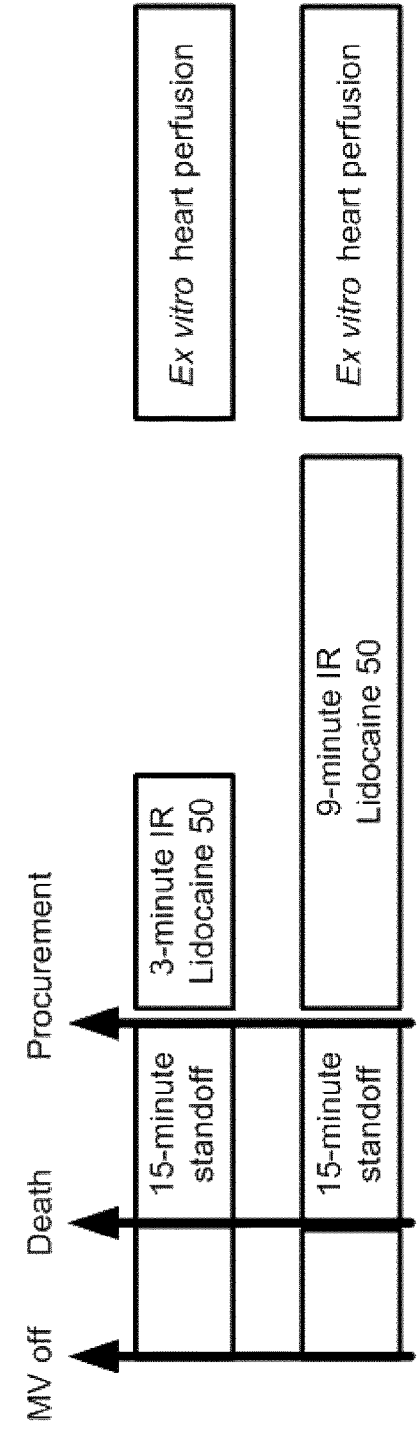

The next study assessed the effects of reducing the lidocaine concentration in the exemplary mildly acidified hypocalcemic oxygenated cardioplegic composition. Accordingly, this study assessed the effects of 3 min or 9 min reperfusion with an exemplary mildly acided (pH 6.9) hypocalcemic (220 µmol/L $Ca^{2+}$) oxygenated cardioplegic solution at 35° C. containing 400 µmol/L adenosine and 50 µmol/L lidocaine (FIG. 28).

Twelve pigs were separated into two groups and then euthanized following standard protocols and medical ethics procedures following the schematic flowchart shown in FIG. 25. Immediately after procurement of each heart was completed, each heart was installed into a Quest MPS®2 Myocardial Protection System. The harvested hearts from the first group of pigs were perfused for 3 minutes with the exemplary mildly acidic hypocalcemic oxygenated cardioplegic composition warmed to 35° C. prior to commencing the reperfusion process for 3 min. The harvested hearts from the second group of pigs were perfused for 9 minutes with the exemplary mildly acidic hypocalcemic oxygenated cardioplegic composition that was warmed to 35° C. prior to commencing the reperfusion process.

The aortic perfusion pressure, coronary artery flow, and myocardial temperature were constantly monitored and recorded by the MPS®2 apparatus during the 3-minute initial reperfusion period. Blood gas samples were measured at 0, 30, 60, 120, and 180 seconds of the initial reperfusion period to collect data pertaining to changes occurring the partial pressure of $O_2$ ($PaO_2$), partial pressure of $CO_2$ ($PaCO_2$), pH levels, electrolyte levels, lactate levels among others.

After the initial 3-minute reperfusion period or the initial 9-minute reperfusion period was completed, each heart was removed from the Quest MPS®2 apparatus and transferred into an ex vivo heart perfusion (EVHP) apparatus where it was perfused with a constantly flowing supply of a blood-STEEN solution mixture (Hb 45 g/L; XVIVO Perfusion Inc., Englewood, Colo., USA) wherein its systolic function was restored and maintained in a Landorff mode at a normothermic temperature of 35° C. for 1 h, 3 h, and 5 h. The aortic pressure and heart rate were constantly monitored and processed using the LABCHART® software. At 1 h of perfusion with the blood-STEEN solution mixture in the EVHP apparatus, each heart was transitioned from the Langendorff mode to a working mode by bringing the left atrial pressure from 0 to 8 mmHg and pacing the heart at 100 bpm. Cardiac output, coronary blood flow, aortic root, and coronary sinus blood gases were measured, and cardiac function was assessed with a pressure-volume loop catheter. After these measurements were completed, each heart was immediately returned to the Langendorff mode for an additional 2 h, after which the measurements were repeated (i.e., 3 h after removal from reperfusion). After these measurements were completed, each heart was immediately returned to the Langendorff mode for an additional 2 h, after which the measurements were repeated (i.e., 5 h after removal from reperfusion).

Figure 29:
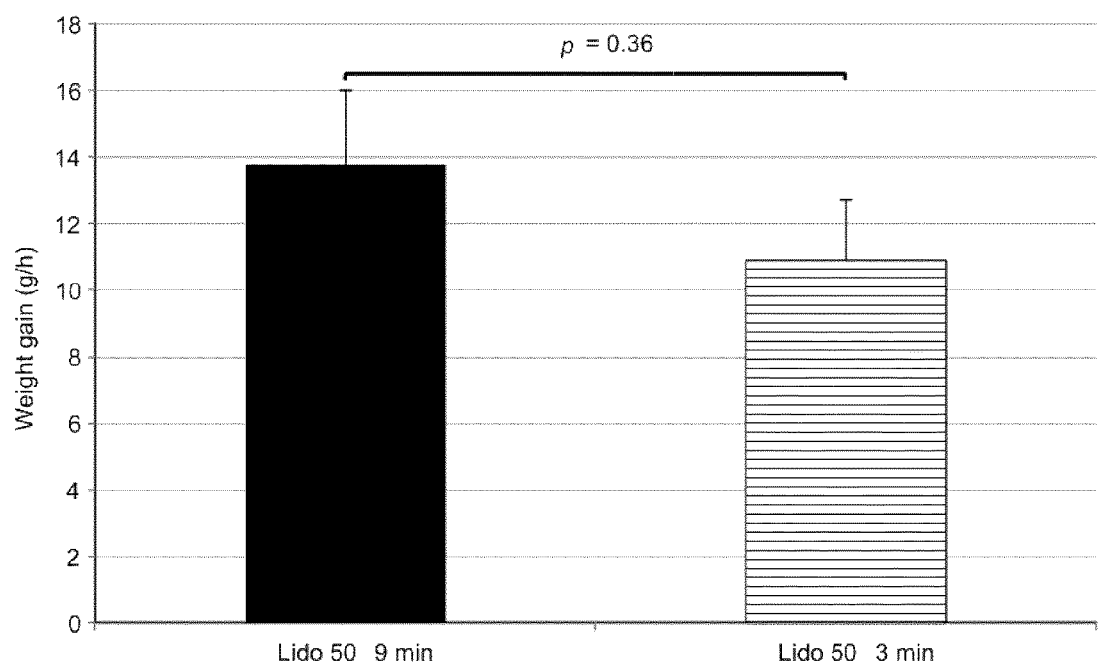
FIG. 29 is a chart showing the effects of extended initial reperfusion with a cardioplegic solution having a reduced concentration of anesthetic on weight gain in reperfused harvested hearts.

FIG. 29 shows that there weren't any significant differences in myocardial edema occurring in the hearts initially reperfused for 9 min compared with hearts perfused for 3 min in the exemplary mildly acidic hypocalcemic oxygenated cardioplegic composition containing 400 µmol/L adenosine and 50 µmol/L lidocaine.

Figure 30:
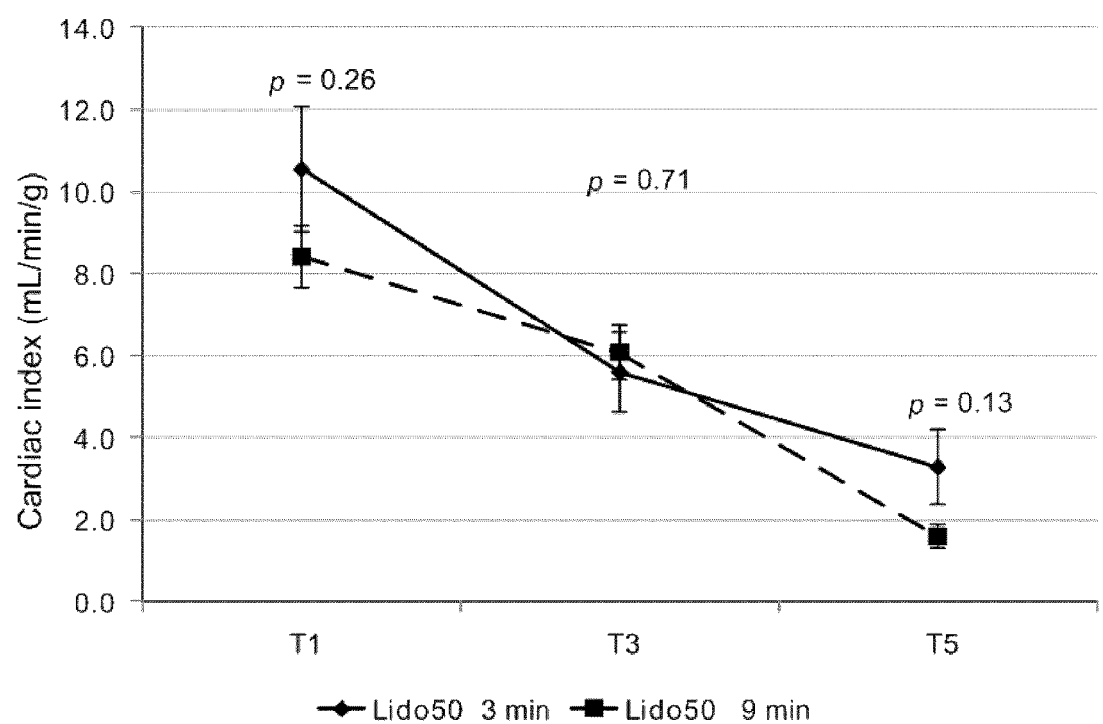
FIG. 30 is a chart showing the effects of extended initial reperfusion with a cardioplegic solution having a reduced concentration of anesthetic on myocardial function of harvested hearts.

FIG. 30 shows that prolonging the initial reperfusion period from 3 min to 9 min in the exemplary mildly acidic hypocalcemic oxygenated cardioplegic composition containing 400 µmol/L adenosine and 50 µmol/L lidocaine, did not have detrimental effects on the functional recovery of hearts perfused for 1 h, 3 h, 5 h after reperfusion.

Figure 31:
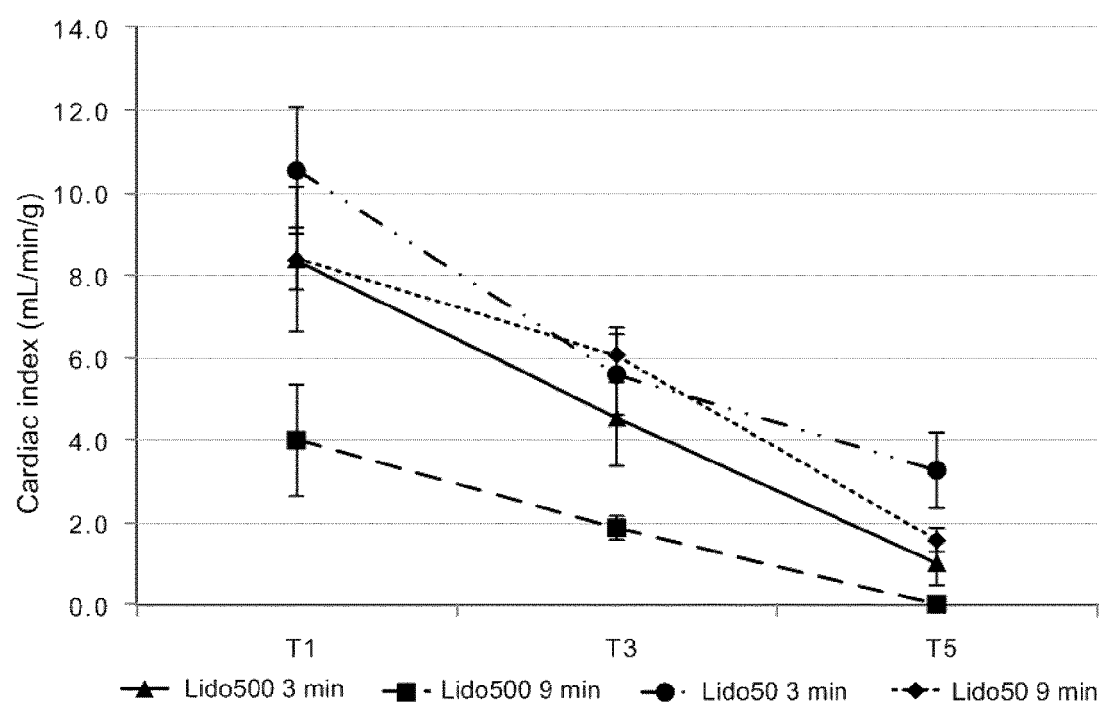
FIG. 31 is a chart showing the effects of anesthetic concentrations in cardioplegic solutions on myocardial function of reperfused harvested hearts.

FIG. 31 combines myocardial functional data from Part 1 (FIG. 27) and Part 2 (FIG. 30), wherein it is apparent that the 500 µmol/L concentration of lidocaine in the cardioplegic compositions used for initial ex vivo post-harvest reperfusion has debilitating effects of donor hearts. This data also demonstrates that prolonging the initial reperfusion period beyond 3 minutes is not beneficial for restoration of homeostatis and cardiac function in harvested donor hearts.

The data presented herein indicate that a suitable composition for a cardioplegic solution for initial ex vivo reperfusion of donor hearts prior to commencing perfusion, is shown in Table 1.

TABLE 1

| Constituent | µmol/L | IU/L | mmol/L |
|---|---|---|---|
| Adenosine | 400 | | |
| Lidocaine | 50 | | |
| Glucose | | | 10.00 |
| NaCl | | | 131.80 |
| KCl | | | 5.90 |
| $NaHCO_3$ | | | 14.00 |
| $NaH_2PO_4$ | | | 1.20 |
| $CaCl_2$ | | | 0.22 |
| $MgCl_2$ | | | 13.00 |
| Insulin | | 10 | |
| D-Mannitol | | | 120.00 |
| Pyruvate | | | 1.00 |
| Reduced glutathione | | | 3.00 |

The invention claimed is:
1. A cardioplegic composition comprising:
400 µmol/L of adenosine;
50 µmol/L of lidocaine;
10.0 mmol/L of glucose;
131.8 mmol/L of NaCl;
5.9 mmol/L of KCl;
14.0 mmol/L of $NaHCO_3$;
1.2 mmol/L of $NaH_2PO_4$;
0.22 mmol/L of $CaCl_2$;
13.0 mmol/L of $MgCl_2$;
10.0 IU/L of insulin
120.0 mmol/L of D-mannitol;
1.0 mmol/L of pyruvate; and
3.0 mmol/L of reduced glutathione, wherein the cardioplegic composition has a pH of 6.6 to 6.9.

2. A method comprising:
bathing and reperfusing a donor heart in the cardioplegic composition of claim 1 immediately after procurement of the donor heart, wherein said cardioplegic composition is oxygenated and warmed to about 35° C. prior to use.

3. The cardioplegic composition of claim 1, wherein the pH is 6.9.

4. The method of claim 2, wherein the pH of the cardioplegic composition is 6.9.

5. The method of claim 2, comprising bathing the donor heart in the oxygenated and warmed cardioplegic composition during procurement of the donor heart.

6. The method of claim 5, wherein the pH of the cardioplegic composition is 6.9.

* * * * *